United States Patent
Lund et al.

(10) Patent No.: US 8,774,942 B2
(45) Date of Patent: Jul. 8, 2014

(54) TISSUE ANCHOR

(75) Inventors: Robert E. Lund, St. Michael, MN (US); John Jason Buysman, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 13/431,594

(22) Filed: Mar. 27, 2012

(65) Prior Publication Data

US 2012/0310317 A1    Dec. 6, 2012

Related U.S. Application Data

(63) Continuation of application No. 12/558,143, filed on Sep. 11, 2009, now abandoned, and a continuation-in-part of application No. 12/170,582, filed on Jul. 10, 2008, now abandoned.

(60) Provisional application No. 61/096,387, filed on Sep. 12, 2008, provisional application No. 61/160,765, filed on Mar. 17, 2009, provisional application No. 60/948,908, filed on Jul. 10, 2007.

(51) Int. Cl.
    *A61N 1/00*    (2006.01)

(52) U.S. Cl.
    USPC ........................................................ 607/126

(58) Field of Classification Search
    USPC ........... 607/115–116, 119, 126–131, 42, 142, 607/152
    See application file for complete search history.

(56) References Cited

U.S. PATENT DOCUMENTS

| | | |
|---|---|---|
| 3,628,538 A | 12/1971 | Vincent et al. |
| 3,640,284 A | 2/1972 | De Langis |
| 3,646,940 A | 3/1972 | Timm et al. |

(Continued)

FOREIGN PATENT DOCUMENTS

| | | |
|---|---|---|
| DE | 8506522.6 U1 | 4/1985 |
| EP | 0245547 | 11/1987 |

(Continued)

OTHER PUBLICATIONS

European Search Report and Written Opinion of 06011641.5 completed Aug. 21, 2006.

(Continued)

*Primary Examiner* — Christopher D Koharski
*Assistant Examiner* — Roland Dinga
(74) *Attorney, Agent, or Firm* — Brian D. Kaul; Westman, Champlin & Koehler, P.A.

(57) ABSTRACT

Embodiments of the invention generally relate to an anchor used to secure a position of a device or component relative to internal tissue of a patient and prevent migration of the component relative to the tissue of the patient. In one embodiment, the anchor is combined with an electrode lead that is configured for implantation in a patient. The electrode lead comprises a lead body having a proximal end and a distal end, a stimulating electrode and the anchor. The stimulating electrode is attached to the lead body at the distal end. The anchor is attached to the distal end of the lead body. In one embodiment, the anchor comprises a plurality of fiber loops each including a fiber having first and second ends attached to the lead body, and an intermediate portion between the first and second ends that is displaced from the lead body.

6 Claims, 19 Drawing Sheets

(56) References Cited

U.S. PATENT DOCUMENTS

| | | | |
|---|---|---|---|
| 3,650,276 A | 3/1972 | Burghele et al. | |
| 3,662,758 A | 5/1972 | Glover | |
| 3,667,477 A | 6/1972 | Susset et al. | |
| 3,866,613 A | 2/1975 | Kenny et al. | |
| 3,870,051 A | 3/1975 | Brindley | |
| 3,926,178 A | 12/1975 | Feldzamen | |
| 3,941,136 A | 3/1976 | Bucalo | |
| 3,983,865 A | 10/1976 | Shepard | |
| 3,983,881 A | 10/1976 | Wickham | |
| 3,999,555 A | 12/1976 | Person | |
| 4,010,758 A | 3/1977 | Rockland et al. | |
| 4,023,574 A | 5/1977 | Nemec | |
| 4,030,509 A | 6/1977 | Heilman et al. | |
| 4,044,774 A | 8/1977 | Corbin et al. | |
| 4,106,511 A | 8/1978 | Erlandsson | |
| 4,136,684 A | 1/1979 | Scattergood et al. | |
| 4,139,006 A | 2/1979 | Corey | |
| 4,153,059 A | 5/1979 | Fravel et al. | |
| 4,157,087 A | 6/1979 | Miller et al. | |
| 4,165,750 A | 8/1979 | Aleev et al. | |
| 4,177,819 A | 12/1979 | Kofsky et al. | |
| 4,222,377 A | 9/1980 | Burton | |
| 4,290,420 A | 9/1981 | Manetta | |
| 4,387,719 A | 6/1983 | Plevnik et al. | |
| 4,402,328 A | 9/1983 | Doring | |
| 4,406,288 A | 9/1983 | Horwinski et al. | |
| 4,414,986 A | 11/1983 | Dickhudt et al. | |
| 4,419,819 A * | 12/1983 | Dickhudt et al. | 29/857 |
| 4,431,001 A | 2/1984 | Hakansson et al. | |
| 4,457,299 A | 7/1984 | Cornwell | |
| 4,492,233 A | 1/1985 | Petrofsky et al. | |
| 4,515,167 A | 5/1985 | Hochman | |
| 4,519,404 A * | 5/1985 | Fleischhacker | 607/126 |
| 4,542,753 A | 9/1985 | Brenman et al. | |
| 4,550,737 A | 11/1985 | Osypka | |
| 4,568,339 A | 2/1986 | Steer | |
| 4,569,351 A | 2/1986 | Tang | |
| 4,571,749 A | 2/1986 | Fischell | |
| 4,580,578 A | 4/1986 | Barsom | |
| 4,585,005 A | 4/1986 | Lue et al. | |
| 4,590,949 A | 5/1986 | Pohndorf | |
| 4,602,624 A | 7/1986 | Naples et al. | |
| 4,607,639 A | 8/1986 | Tanagho et al. | |
| 4,628,942 A | 12/1986 | Sweeney et al. | |
| 4,669,488 A * | 6/1987 | Hess | 607/126 |
| 4,688,575 A | 8/1987 | DuVall | |
| 4,703,755 A | 11/1987 | Tanagho et al. | |
| 4,731,083 A | 3/1988 | Fischell | |
| 4,739,764 A | 4/1988 | Lue et al. | |
| 4,750,494 A | 6/1988 | King | |
| 4,771,779 A | 9/1988 | Tanagho et al. | |
| 4,785,828 A | 11/1988 | Maurer | |
| 4,881,526 A | 11/1989 | Johnson et al. | |
| 4,913,164 A | 4/1990 | Greene et al. | |
| 4,941,874 A | 7/1990 | Sandow et al. | |
| 5,013,292 A | 5/1991 | Lemay | |
| 5,019,032 A | 5/1991 | Robertson | |
| 5,082,006 A | 1/1992 | Jonasson | |
| 5,094,242 A | 3/1992 | Gleason et al. | |
| 5,103,835 A | 4/1992 | Yamada et al. | |
| 5,112,344 A | 5/1992 | Petros | |
| 5,193,539 A | 3/1993 | Schulman et al. | |
| 5,193,540 A | 3/1993 | Schulman et al. | |
| 5,199,430 A | 4/1993 | Fang et al. | |
| 5,285,781 A | 2/1994 | Brodard | |
| 5,291,902 A | 3/1994 | Carman | |
| 5,312,439 A | 5/1994 | Loeb | |
| 5,324,316 A | 6/1994 | Schulman et al. | |
| 5,324,324 A | 6/1994 | Vachon et al. | |
| 5,324,327 A * | 6/1994 | Cohen | 607/122 |
| 5,330,507 A | 7/1994 | Schwartz | |
| 5,344,439 A | 9/1994 | Otten | |
| 5,358,514 A | 10/1994 | Schulman et al. | |
| 5,405,367 A | 4/1995 | Schulman et al. | |
| 5,411,548 A | 5/1995 | Carman | |
| 5,417,226 A | 5/1995 | Juma | |
| 5,423,329 A | 6/1995 | Ergas | |
| 5,452,719 A | 9/1995 | Eisman et al. | |
| 5,484,445 A | 1/1996 | Knuth | |
| 5,518,504 A | 5/1996 | Polyak | |
| 5,520,606 A | 5/1996 | Schoolman et al. | |
| 5,562,717 A | 10/1996 | Tippey et al. | |
| 5,569,351 A | 10/1996 | Menta et al. | |
| 5,571,148 A | 11/1996 | Loeb et al. | |
| 5,611,515 A | 3/1997 | Benderev et al. | |
| 5,611,768 A | 3/1997 | Tutrone, Jr. | |
| 5,634,462 A | 6/1997 | Tyler et al. | |
| 5,702,428 A | 12/1997 | Tippey et al. | |
| 5,752,978 A | 5/1998 | Chancellor | |
| 5,755,767 A * | 5/1998 | Doan et al. | 607/126 |
| 5,807,397 A | 9/1998 | Barreras | |
| 5,824,027 A | 10/1998 | Hoffer et al. | |
| 5,833,595 A | 11/1998 | Lin | |
| 5,842,478 A | 12/1998 | Benderev et al. | |
| 5,860,425 A | 1/1999 | Benderev et al. | |
| 5,899,909 A | 5/1999 | Claren et al. | |
| 5,927,282 A | 7/1999 | Lenker et al. | |
| 5,931,864 A | 8/1999 | Chastain et al. | |
| 5,954,761 A | 9/1999 | Machek et al. | |
| 5,957,920 A | 9/1999 | Baker | |
| 5,957,965 A | 9/1999 | Moumane et al. | |
| 5,978,712 A | 11/1999 | Suda et al. | |
| 5,984,854 A | 11/1999 | Ishikawa et al. | |
| 6,002,964 A | 12/1999 | Feler et al. | |
| 6,026,326 A | 2/2000 | Bardy | |
| 6,027,456 A | 2/2000 | Feler et al. | |
| 6,039,686 A | 3/2000 | Kovac | |
| 6,042,534 A | 3/2000 | Gellman et al. | |
| 6,051,017 A | 4/2000 | Loeb et al. | |
| 6,055,456 A | 4/2000 | Gerber | |
| 6,061,596 A | 5/2000 | Richmond et al. | |
| 6,104,955 A | 8/2000 | Burgeois | |
| 6,104,960 A | 8/2000 | Duysens et al. | |
| 6,110,101 A | 8/2000 | Tihon et al. | |
| 6,131,575 A | 10/2000 | Lenker et al. | |
| 6,135,945 A | 10/2000 | Sultan | |
| 6,141,594 A | 10/2000 | Flynn et al. | |
| 6,161,029 A | 12/2000 | Spreigl et al. | |
| 6,178,356 B1 * | 1/2001 | Chastain et al. | 607/128 |
| 6,185,452 B1 | 2/2001 | Schulman et al. | |
| 6,208,894 B1 | 3/2001 | Schulman et al. | |
| 6,240,315 B1 | 5/2001 | Mo et al. | |
| 6,240,316 B1 | 5/2001 | Richmond et al. | |
| 6,243,607 B1 | 6/2001 | Mintchev et al. | |
| 6,266,557 B1 | 7/2001 | Roe et al. | |
| 6,266,564 B1 | 7/2001 | Hill et al. | |
| 6,304,786 B1 | 10/2001 | Heil et al. | |
| 6,328,686 B1 | 12/2001 | Kovac | |
| 6,341,236 B1 | 1/2002 | Osorio et al. | |
| 6,354,991 B1 | 3/2002 | Gross et al. | |
| 6,360,750 B1 | 3/2002 | Gerber et al. | |
| 6,366,814 B1 | 4/2002 | Boveja et al. | |
| 6,382,214 B1 | 5/2002 | Raz et al. | |
| 6,397,109 B1 | 5/2002 | Cammilli et al. | |
| 6,407,308 B1 | 6/2002 | Roe et al. | |
| 6,418,930 B1 | 7/2002 | Fowler | |
| 6,505,082 B1 | 1/2003 | Scheiner et al. | |
| 6,572,543 B1 * | 6/2003 | Christopherson et al. | 600/300 |
| 6,582,441 B1 | 6/2003 | He et al. | |
| 6,600,956 B2 | 7/2003 | Maschino et al. | |
| 6,612,977 B2 | 9/2003 | Staskin et al. | |
| 6,641,524 B2 | 11/2003 | Kovac | |
| 6,650,943 B1 | 11/2003 | Whitehurst et al. | |
| 6,652,449 B1 | 11/2003 | Gross et al. | |
| 6,652,450 B2 | 11/2003 | Neisz et al. | |
| 6,658,297 B2 | 12/2003 | Loeb | |
| 6,659,936 B1 | 12/2003 | Furness et al. | |
| 6,712,772 B2 | 3/2004 | Cohen et al. | |
| 6,735,474 B1 | 5/2004 | Loeb et al. | |
| 6,745,079 B2 | 6/2004 | King | |
| 6,802,807 B2 | 10/2004 | Anderson et al. | |
| 6,862,480 B2 | 3/2005 | Cohen et al. | |
| 6,896,651 B2 | 5/2005 | Gross et al. | |
| 6,911,003 B2 | 6/2005 | Anderson et al. | |

(56) References Cited

U.S. PATENT DOCUMENTS

| | | |
|---|---|---|
| 6,941,171 B2 | 9/2005 | Mann et al. |
| 6,952,613 B2 | 10/2005 | Swoyer et al. |
| 6,964,643 B2 | 11/2005 | Hovland et al. |
| 6,964,699 B1 | 11/2005 | Carns et al. |
| 6,971,393 B1 | 12/2005 | Mamo et al. |
| 7,079,882 B1 | 7/2006 | Schmidt |
| 7,120,499 B2 | 10/2006 | Thrope et al. |
| 7,319,905 B1 | 1/2008 | Morgan et al. |
| 7,328,068 B2 | 2/2008 | Spinelli et al. |
| 7,330,764 B2 | 2/2008 | Swoyer et al. |
| 7,343,202 B2 | 3/2008 | Mrva et al. |
| 7,376,467 B2 | 5/2008 | Thrope et al. |
| 7,376,468 B2 | 5/2008 | King et al. |
| 7,613,516 B2 | 11/2009 | Cohen et al. |
| 7,628,795 B2 | 12/2009 | Karwoski et al. |
| 7,647,113 B2 | 1/2010 | Wirbisky et al. |
| 7,725,197 B2 | 5/2010 | Soltis et al. |
| 7,771,345 B1 | 8/2010 | O'Donnell |
| 8,019,443 B2 | 9/2011 | Schleicher et al. |
| 8,052,731 B2 | 11/2011 | Soltis et al. |
| 2001/0002441 A1 | 5/2001 | Boveja |
| 2001/0003799 A1 | 6/2001 | Boveja |
| 2001/0018549 A1 | 8/2001 | Scetbon |
| 2002/0055761 A1 | 5/2002 | Mann et al. |
| 2002/0099259 A1 | 7/2002 | Anderson et al. |
| 2002/0161382 A1 | 10/2002 | Neisz et al. |
| 2002/0165566 A1 | 11/2002 | Ulmsten |
| 2003/0018365 A1 | 1/2003 | Loeb |
| 2003/0023296 A1 | 1/2003 | Osypka |
| 2003/0028232 A1 | 2/2003 | Camps et al. |
| 2003/0060868 A1 | 3/2003 | Janke et al. |
| 2003/0100930 A1 | 5/2003 | Cohen et al. |
| 2003/0171644 A1 | 9/2003 | Anderson et al. |
| 2003/0199961 A1 | 10/2003 | Bjorklund et al. |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0039453 A1 | 2/2004 | Anderson et al. |
| 2004/0059392 A1 | 3/2004 | Parramon et al. |
| 2004/0068203 A1 | 4/2004 | Gellman et al. |
| 2004/0093053 A1 | 5/2004 | Gerber et al. |
| 2004/0242956 A1 | 12/2004 | Scorvo |
| 2004/0248979 A1 | 12/2004 | Brettman et al. |
| 2005/0038489 A1 | 2/2005 | Grill |
| 2005/0043580 A1 | 2/2005 | Watschke et al. |
| 2005/0065395 A1 | 3/2005 | Mellier |
| 2005/0113877 A1 | 5/2005 | Spinelli et al. |
| 2005/0119710 A1 | 6/2005 | Furness et al. |
| 2005/0143618 A1 | 6/2005 | Anderson et al. |
| 2005/0149156 A1 | 7/2005 | Libbus et al. |
| 2005/0216069 A1 | 9/2005 | Cohen et al. |
| 2005/0228346 A1 | 10/2005 | Goode et al. |
| 2005/0245787 A1 | 11/2005 | Cox et al. |
| 2005/0245874 A1 | 11/2005 | Carrez et al. |
| 2005/0250977 A1 | 11/2005 | Montpetit et al. |
| 2005/0283235 A1 | 12/2005 | Kugler et al. |
| 2006/0004421 A1 | 1/2006 | Bennett et al. |
| 2006/0004429 A1 | 1/2006 | Mrva et al. |
| 2006/0149345 A1 | 7/2006 | Boggs, II et al. |
| 2006/0173520 A1 | 8/2006 | Olson |
| 2006/0241733 A1 | 10/2006 | Zhang et al. |
| 2006/0287571 A1 | 12/2006 | Gozzi et al. |
| 2007/0021650 A1 | 1/2007 | Rocheleau et al. |
| 2007/0043416 A1 | 2/2007 | Callas et al. |
| 2007/0100411 A1 | 5/2007 | Bonde |
| 2007/0123952 A1 | 5/2007 | Strother et al. |
| 2007/0179559 A1 | 8/2007 | Giftakis et al. |
| 2007/0185541 A1 | 8/2007 | DiUbaldi et al. |
| 2007/0239224 A1 | 10/2007 | Bennett et al. |
| 2007/0253997 A1 | 11/2007 | Giftakis et al. |
| 2007/0253998 A1 | 11/2007 | Giftakis et al. |
| 2007/0255333 A1 | 11/2007 | Giftakis et al. |
| 2007/0255341 A1 | 11/2007 | Giftakis et al. |
| 2007/0260288 A1 | 11/2007 | Gross et al. |
| 2007/0265675 A1 | 11/2007 | Lund et al. |
| 2008/0009914 A1 | 1/2008 | Buysman et al. |
| 2008/0071321 A1 | 3/2008 | Boggs, II et al. |
| 2008/0114433 A1 | 5/2008 | Sage et al. |
| 2008/0132969 A1 | 6/2008 | Bennett et al. |
| 2009/0012592 A1 | 1/2009 | Buysman et al. |
| 2009/0043356 A1 | 2/2009 | Longhini et al. |
| 2009/0157091 A1 | 6/2009 | Buysman |
| 2009/0259280 A1 | 10/2009 | Wilkin et al. |
| 2010/0049289 A1 | 2/2010 | Lund et al. |
| 2010/0076254 A1 | 3/2010 | Jimenez et al. |
| 2012/0095478 A1 | 4/2012 | Wang et al. |

FOREIGN PATENT DOCUMENTS

| | | |
|---|---|---|
| EP | 1 661 600 A1 | 5/2006 |
| EP | 1119314 B1 | 6/2006 |
| GB | 2309388 | 7/1997 |
| WO | 9012617 | 11/1990 |
| WO | 9604955 | 2/1996 |
| WO | 9632916 | 10/1996 |
| WO | 9817190 A2 | 4/1998 |
| WO | 0000082 A1 | 1/2000 |
| WO | 0019940 | 4/2000 |
| WO | 0239890 A2 | 5/2002 |
| WO | 02069781 | 9/2002 |
| WO | 02078592 | 10/2002 |
| WO | 03002192 | 1/2003 |
| WO | 2006047833 | 5/2006 |
| WO | 2007025354 A1 | 3/2007 |
| WO | 2007097994 A2 | 8/2007 |
| WO | 2007145913 A1 | 12/2007 |
| WO | 2007126632 A3 | 3/2008 |
| WO | 2009026078 A2 | 2/2009 |
| WO | 2010107751 A2 | 9/2010 |

OTHER PUBLICATIONS

International Search Report and Written Opinion of PCT/US2007/004474 filed on Feb. 22, 2007.
U.S. Appl. No. 60/779,219, filed Mar. 3, 2006.
International Search Report and Written Opinion of PCT/US2007/000112 filed Jan. 3, 2007.
U.S. Appl. No. 12/406,434, filed Mar. 18, 2009.
U.S. Appl. No. 61/160,765, filed Mar. 17, 2009.
U.S. Appl. No. 60/578,742, filed Jun. 10, 2004.
Caldwell, K.P.S. "Electrical Stimulation.", Sphincter Research Unit, Royal Devon and Exeter Hospital, Exeter (England), Urol. Int. 29: 225, 1974. (1 page).
Caldwell, K.P.S. "The Use of Electrical Stimulation in Urinary Retention and Incontinence [Abridged]." Section of Urology, vol. 61, pp. 35-39, Jul. 1968.
Caldwell, K.P.S. et al. "Urethral Pressure Recordings in Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.
U.S. Appl. No. 11/746,476, filed May 9, 2007.
Notification of the First Office Action from corresponding Chinese patent application No. 200780007709.2, mailed Sep. 27, 2010.
Dietz et al., Mechanical Properties of Urogynecologic Implant Materials, Int. Urogynecol J. (2003) 14:239-243.
Iglesia et al., "The Use of Mesh in Gynecologic Surgery", Int. Urogynecol J. (1997) 8:105-115.
Office Action from U.S. Appl. No. 12/170,582, mailed Nov. 24, 2010.
Partial European Search Report from European Patent Application No. 10176162.5, mailed Jan. 21, 2011.
Yamamoto et al., "Optimal parameters for effective electrical stimulation of the anal sphincters in a child with fecal incontinence: preliminary report," Pediatr Surg Int (1993) 8:132-137.
Yamanishi et al., "Electrical Stimulation for Stress Incontinence", Int. Urogynecol J (1998) 9:281-290 Springer-Verlag London Ltd.
Office Action from U.S. Appl. No. 12/170,582 dated Apr. 12, 2011.

(56) References Cited

OTHER PUBLICATIONS

Extended European Search Report and Search Opinion for European patent application No. EP 10176162.5 dated Apr. 28, 2011.

International Search Report and Written Opinion for PCT/US2011/023677 dated Apr. 21, 2011.

Prosecution documents associated with U.S. Appl. No. 12/558,143 including: Office Action mailed Dec. 13, 2011; Final Office Action mailed Sep. 29, 2011; Office Action mailed Jun. 20, 2011; and Requirement for Restriction/Election mailed May 12, 2011.

Prosecution documents associated with U.S. Appl. No. 12/170,582 including: Advisory Action mailed Jan. 27, 2012; Final Office Action mailed Nov. 21, 2011; Office Action mailed Aug. 2, 2011; Advisory Action mailed Jun. 16, 2011.

European Patent Office Communication from European Patent Application No. 10710501.7. dated Oct. 12, 2012.

Examiner's First Report from Australian Patent Application No. 2010226813, dated Sep. 18, 2012.

International Search Report and Written Opinion of PCT/US2010/027419, mailed Sep. 27, 2010.

\* cited by examiner

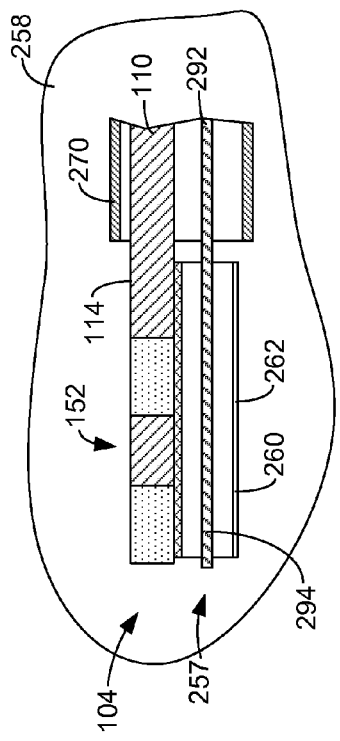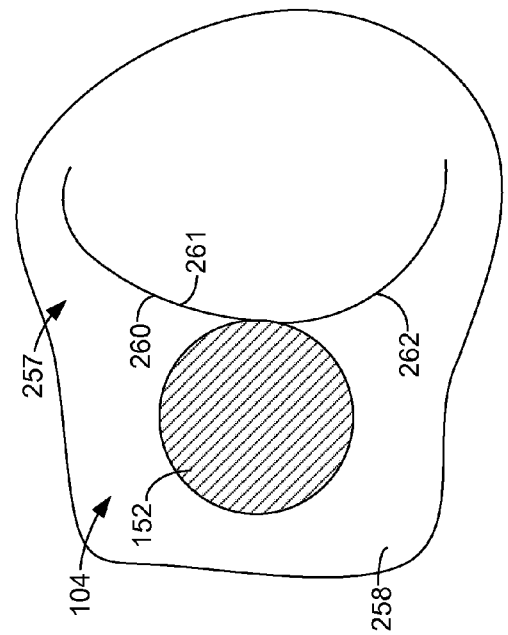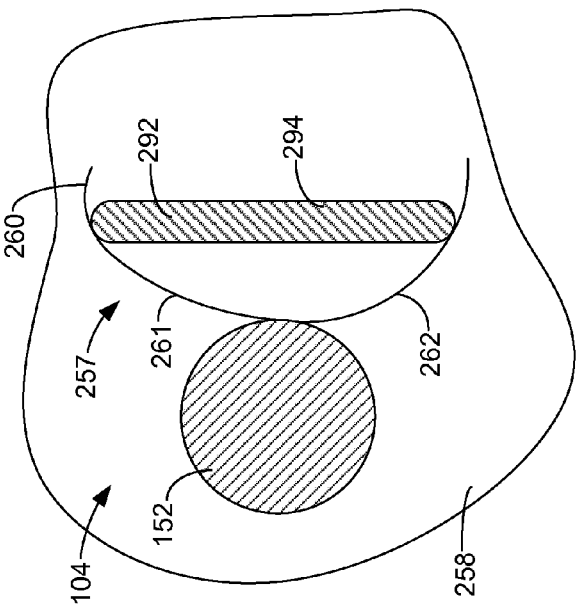

TISSUE ANCHOR

CROSS-REFERENCE TO RELATED APPLICATIONS

The present application is a continuation of U.S. application Ser. No. 12/558,143 filed Sep. 11, 2009 now abandoned, which claims the benefit of U.S. provisional patent application Ser. Nos. 61/096,387 filed Sep. 12, 2008 and 61/160,765 filed Mar. 17, 2009 and is a continuation-in-part of U.S. application Ser. No. 12/170,582 filed Jul. 10, 2008 now abandoned, which in turn claims the benefit of U.S. provisional patent application Ser. No. 60/948,908, filed Jul. 10, 2007. The content of each of the above-referenced applications, is hereby incorporated by reference in its entirety.

FIELD OF THE INVENTION

Embodiments of the present invention generally relate to an anchor that facilitates securing devices or components to internal tissue of a patient and preventing migration of the devices or components from their intended location relative to the tissue of the patient.

BACKGROUND OF THE INVENTION

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. Electrical signals are applied to the desired pelvic tissue of the patient through the electrode leads in order to treat the condition of the patient. The electrode leads are typically secured to the tissue using an anchor in the form of a helical coil. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

Urinary incontinence in women has been treated by a surgical method involving the placement of a sling to stabilize or support the bladder neck or urethra of the patient. Varieties of sling procedures are described in U.S. Pub. No. 2002-0161382 A1, which is incorporated herein by reference in its entirety. One type of sling procedure is a pubovaginal sling procedure, which is a minimally invasive surgical method involving the placement (e.g. by the use of a Stamey needle or other ligature carrier) of a sling to stabilize or support the bladder neck or urethra. This procedure does not utilize bone anchors. Rather the sling is anchored in the abdominal or rectus fascia.

U.S. Pub. No. 2007-0260288 A1, which is incorporated herein by reference in its entirety, generally describes a combination of the above devices. One or more electrodes are attached to a mechanical support, such as a sling, that supports a portion of the urethra of the patient. The electrodes are configured to contact tissue of the patient when the mechanical support is implanted in the patient. A control unit drives the electrodes to apply a current to the tissue that treats a pelvic condition of the patient.

The above-describe devices utilize anchors to secure components of the devices, such as electrode leads and/or mechanical supports, in tissue of the patient. It is desirable, for example, that such anchors prevent relative movement between the anchor and the tissue in which the anchor in embedded, are easy to install in the tissue, avoid damaging the tissue during the implantation procedure, operate as electrical stimulators, can be temporarily moved relative to the tissue without significant restriction by the anchor during installation, can be removed without significantly damaging the tissue, and/or have other features or benefits recognized by those skilled in the art.

SUMMARY OF THE INVENTION

Embodiments of the invention generally relate to an anchor used to secure a position of a device or component relative to internal tissue of a patient and prevent migration of the component relative to the tissue of the patient. In one embodiment, the anchor is combined with an electrode lead that is configured for implantation in a patient. The electrode lead comprises a lead body having a proximal end and a distal end, a stimulating electrode and the anchor. The stimulating electrode is attached to the lead body at the distal end. The anchor is attached to the distal end of the lead body. In one embodiment, the anchor comprises a plurality of fiber loops each including a fiber having first and second ends attached to the lead body, and an intermediate portion between the first and second ends that is displaced from the lead body. In accordance with another embodiment, the anchor comprises one or more annular protruding elements concentric to the longitudinal axis and including a proximal end attached to the lead body and a distal end displaced from the lead body.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIGS. 37-39 illustrate method steps of deploying the distal end of the electrode lead of FIGS. 35 and 36 within tissue of a patient, in accordance with embodiments of the invention.

DETAILED DESCRIPTION OF ILLUSTRATIVE EMBODIMENTS

Embodiments of the invention are directed to an anchor that facilitates securing devices or components, such as electrode leads, mechanical supports (e.g., meshes, slings), and other devices or components to internal tissue of a patient, and preventing migration of the devices or components from their intended position.

The tissue in which the anchor of the present invention may be use includes adipose tissue, muscle tissue or any other tissue of the patient. In one embodiment, the tissue is located in the pelvic region of the patient. In some embodiments, the tissue, in which the anchor is to be embedded, is targeted for electrical stimulation or is adjacent a desired stimulation target site. Embodiments of the invention comprise the individual embodiments described below and combinations of two or more of the embodiments described below.

Figure 1:
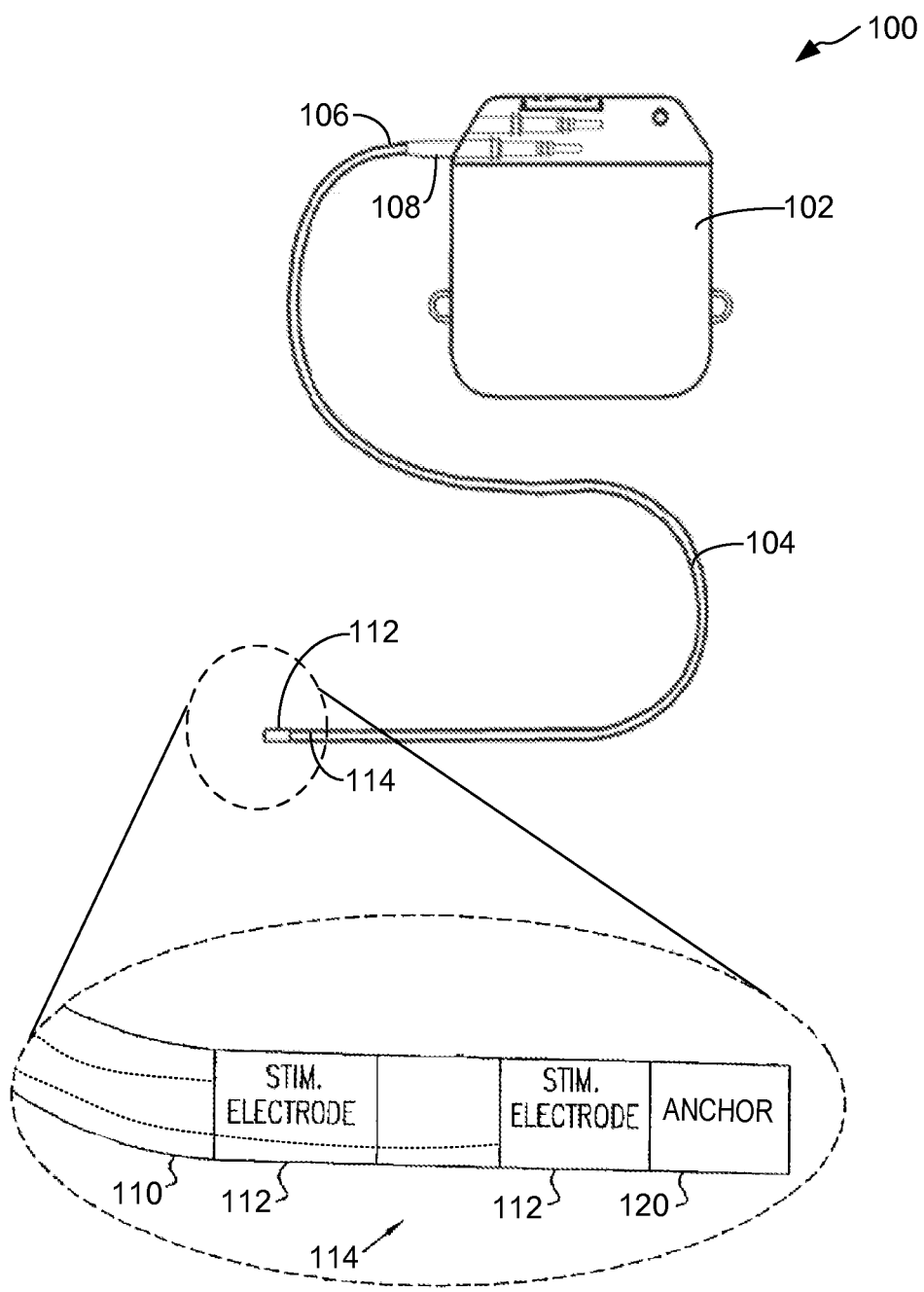
FIG. 1 is a side plan view of an exemplary electronic stimulator device, in accordance with the embodiments of the invention.

Initially, exemplary devices or components with which the anchors of the present invention may be used will be discussed. FIG. 1 is a side plan view of an exemplary electronic stimulator device 100, with which embodiments of the anchors of the present invention may be used. Device 100 is configured for implantation into a pelvic region of a patient to provide muscle and/or nerve stimulation that is used to control and/or treat a pelvic condition of the patient, such as pelvic pain, urinary incontinence, fecal incontinence, erectile dysfunction or other pelvic condition that may be treated through electrical stimulation.

In one embodiment, the device 100 comprises a control unit 102 and one or more electrode leads 104, a proximal end 106 of which is coupled to the control unit 102 via a connector 108. Each electrode lead 104 comprises a lead body 110 and one or more stimulating electrodes 112 at a distal end 114 of the electrode lead 104 or lead body 110. The lead body 110 insulates electrical wires connecting the control unit 102 to the stimulating electrodes 112. The lead body 110 can be in the form of an insulating jacket typically comprising silicone, polyurethane or other flexible, biocompatible electrically insulating material. Additional electrode leads 104 or physiological sensors may be coupled to the control unit 102.

In one embodiment, the control unit 102 comprises circuitry for processing electrical signals received from the one or more stimulating electrodes 112 or physiological sensors. The control unit 102 is also configured to apply an electrical current or waveform to the tissue of the patient that is in contact with the one or more stimulating electrodes 112.

The electrode lead 104 can be anchored to pelvic tissue of the patient (e.g., internal urinary sphincter muscle) by means of a tissue anchor 120, which is formed in accordance with embodiments of the invention described below. The anchor 120 operates to secure the position of the distal end 114 of the electrode lead 104 in the desired tissue of the patient. The anchor 120 can be coupled to the lead body 110 or the stimulating electrode 112 at a location that is proximate to the distal end 114 of the electrode lead 104, for example. In one embodiment, the anchor 120 operates to provide electrical contact between the pelvic tissue of the patient and the one or more stimulation electrodes 112 of the electrode lead 104.

Figure 2:
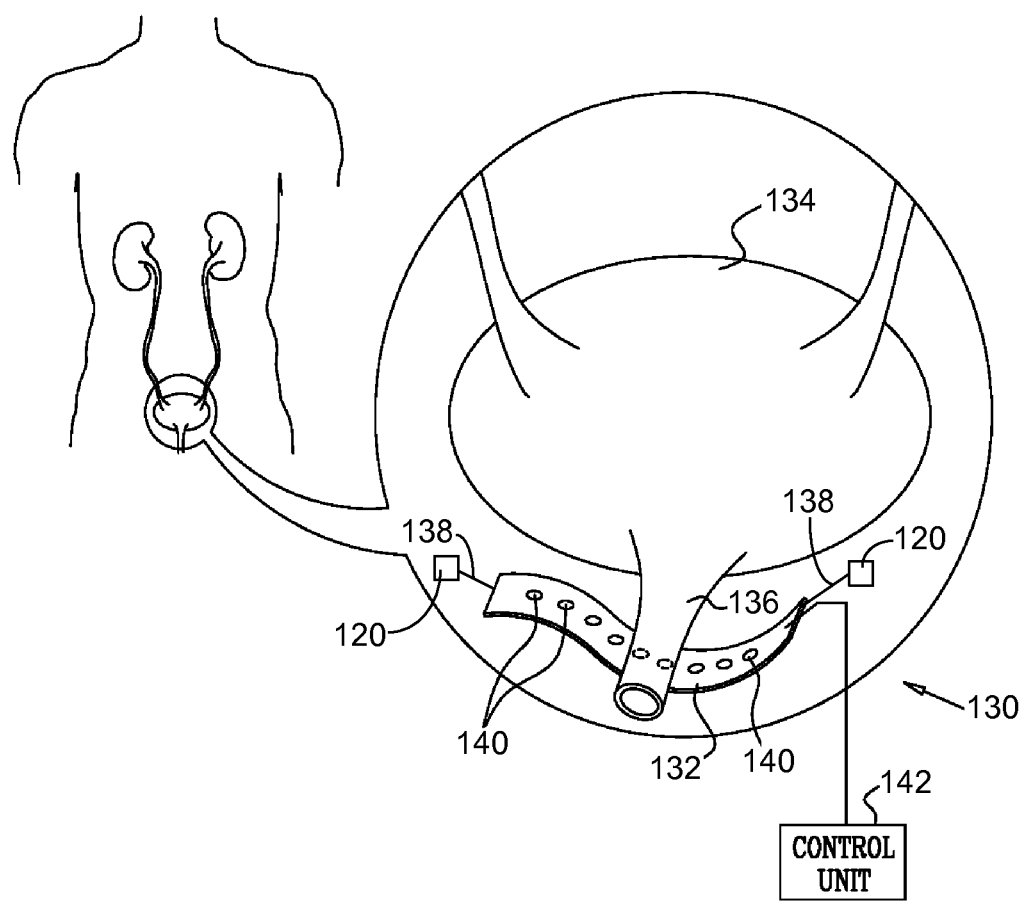
FIG. 2 is a schematic illustration of a pelvic treatment apparatus in accordance with embodiments of the invention.

Another device or component with which embodiments of the anchor 120 may be used is a pelvic treatment apparatus 130, an example of which is illustrated in FIG. 2. The pelvic treatment apparatus 130 can be used to treat, for example, urinary incontinence of a patient, and generally comprises a mechanical support 132, which can be in the form of a mesh or other mechanical support that is installed to provide support to the neck of the bladder 134 or the urethra of the patient, which are generally indicated at 136. The mechanical support can be configured for implantation by any number of known surgical approaches, for example, a suprapubic approach, a transvaginal approach, a retropubic approach, and a transobturator approach.

In one embodiment, the mechanical support is anchored to pelvic tissue of the patient using one or more anchors 120 of the present invention described below. Each anchor 120 can be attached to a cable 138 or directly attached to the mechanical support 132.

In one embodiment, the pelvic treatment apparatus 130 includes one or more stimulating electrodes 140 that are attached to the mechanical support 132 or extend from the mechanical support 132 on electrode leads (not shown), such as those described above with reference to FIG. 1. A control unit 142, located inside or outside of the patient's body, drives the electrodes 140 to apply a current to a pelvic site and treat, for example, stress incontinence, urge incontinence, urge frequency, erectile dysfunction, or other pelvic dysfunctions.

Figure 3:
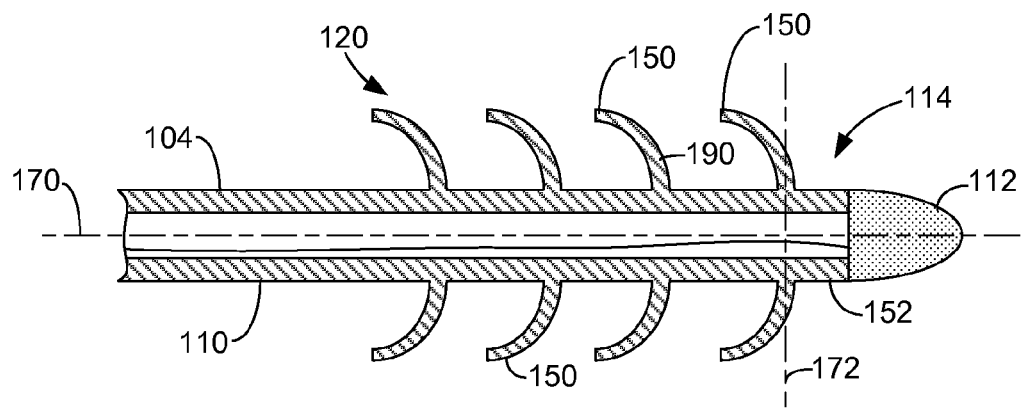
FIGS. 3-5 are cross-sectional views of a distal end of an exemplary electrode lead that includes one or more tissue anchors in accordance with embodiments of the invention.
Figure 4:
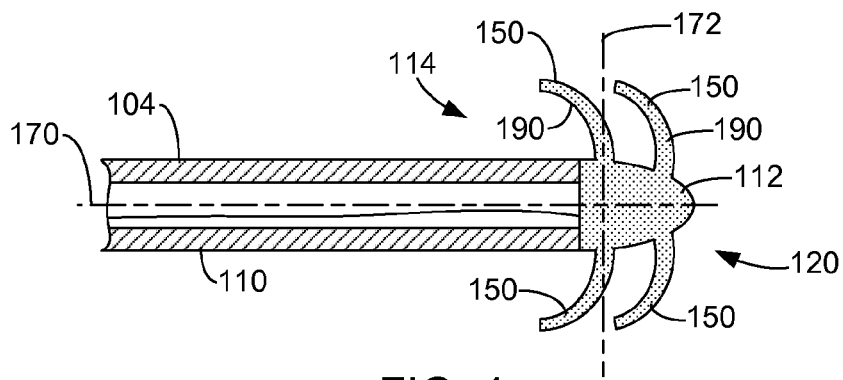
Figure 5:
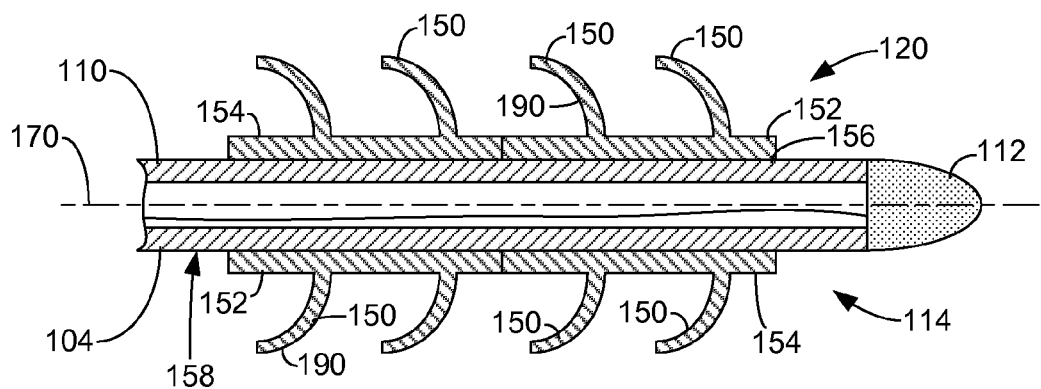

FIGS. 3-5 are cross-sectional views of the distal end 114 of an electrode lead 104 that includes one or more anchors or fixation components 120 in accordance with embodiments of the invention. While FIGS. 3-5 specifically illustrate the anchor 120 in use with the electrode lead 104, it is understood that embodiments of the anchor 120 include its use with other devices and components, such as the mechanical support described above.

Each anchor 120 generally comprises one or more protruding elements 150 that are attached to an anchor body 152. It is understood that although exemplary illustrations of the anchors 120 described below comprise multiple protruding elements 150, it is understood that embodiments of the anchor 120 include anchors having a single protruding element 150 and anchors having different types of protruding elements 150 in accordance with the embodiments described herein.

Multiple embodiments of the anchor 120 that are generally independent of the type of protruding element 150 that is employed will initially be discussed with reference to FIGS. 3-5. Embodiments of the anchor body 152 include the lead body 110 (FIG. 3), the stimulating electrode 112 (FIG. 4), a mechanical support or sling 132 (FIG. 2), a cable 138 (FIG. 2), and a separate component 154 (FIG. 5) that can be attached to the lead body 110 or other component. These embodiments of the anchor body 152 are generally included in each reference to the anchor body 152.

In one embodiment, the anchor body 152 and the protruding elements 150 can be formed of a wide variety of biocompatible implant materials. Suitable materials for an implant include polymerics, and plastics such as polypropylene, polyethylene, nylon, polyester, biocompatible metals or other suitable biocompatible material. In one embodiment, the protruding elements 150 of the stimulating electrode 112 are formed of a metallic conductive material, such as that of the stimulating electrode 112.

In one embodiment, the protruding elements 150 are integral with the anchor body 152, such as the lead body 110 or the stimulating electrode 112, as respectively illustrated in FIGS. 3 and 4. Thus, the protruding elements 150 are either formed along with the formation of the anchor body 152 or are subsequently fused to the anchor body 152 through a welding or other conventional process. In one embodiment, when the protruding elements are integral with the stimulating electrode 112, the stimulating signals generated by the control unit 102 are discharged into the tissue through the electrically conductive protruding elements 150.

In one embodiment, the protruding elements 150 are non-integral to the anchor body 152. That is, the protruding elements 152 are attached to the anchor body 152 using an adhesive, a mechanical fastener or other suitable means.

As mentioned above, one embodiment of the anchor body 152 comprises a component 154 that is used to attach the anchor to the desired electrode body 110, stimulating electrode 112, mechanical support 132 or other component. In one embodiment, the component 154 comprises a hub or sleeve as shown in FIG. 5, to which one or more of the protruding elements 150 are attached. The component 154 can be attached to the lead body 110 (FIG. 5) to the stimulating electrode 112, the mechanical support 132, or other component. The protruding elements 150 can be attached to the component 154 or formed integral therewith.

In one embodiment, the component 154 comprises a cylindrical hub having a bore 156 having a diameter that is slightly larger than the external diameter the component to which it is attached and concentric thereto, an example of which is the lead body 110 shown in FIG. 5. The cylindrical hub 154 is fixedly attached to a desired portion of the lead body 110 or the stimulating electrode 112 using a biocompatible adhesive or other suitable means. In one embodiment, the bore 156 of the cylindrical hub 154 is approximately the same or smaller than the external diameter of the lead body 110 or other component to which it is attached, such that the bore 156 of the cylindrical hub 154 compresses the exterior surface 158 of the lead body 110 with sufficient force to maintain the relative positions of the cylindrical hub 154 and the lead body 110 during, and subsequent to, implantation of the electrode lead 104 in the patient.

Figure 6:
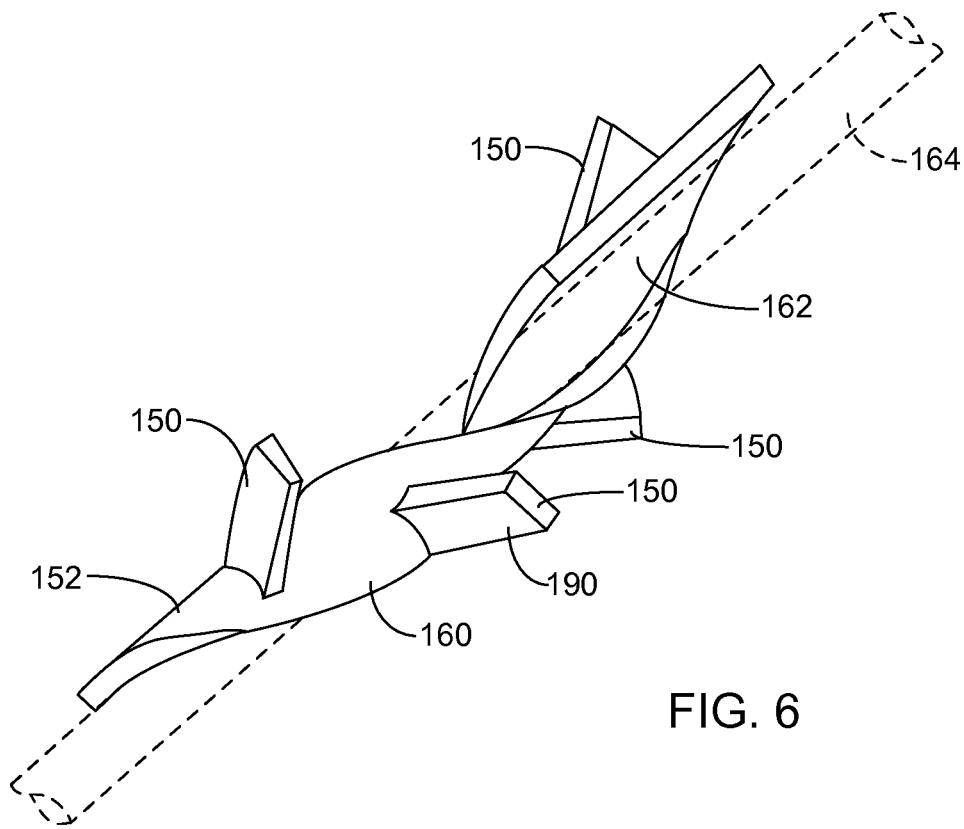
FIG. 6 is an isometric view of an anchor in accordance with embodiments of the invention.

In one embodiment, the anchor body 152 comprises a spiral tube 160, from which the one or more protruding elements 150 extend, as shown in FIG. 6. In one embodiment, the spiral tube 160 wraps around the lead body 110, the stimulating electrode 112, or other component, represented in phantom lines, and is fixed thereto using a biocompatible adhesive or through frictional resistance between the interior surface 162 of the spiral tube 160 and the exterior surface 164 of the lead body or stimulating electrode. As mentioned above, the anchor body 152 can be formed by the stimulating electrode 112. Thus, it is understood that, in a related embodiment, the stimulating electrode 112 is formed like the anchor body 152 with spiral tube 160.

The following discussion of the location and orientation of the protruding elements 150 in accordance with embodiments of the invention applies to the embodiments described above and is generally independent of the type of anchor body 152, to which the protruding elements 150 are attached. In one embodiment, at least some of the protruding elements 150 are displaced from each other along the longitudinal axis of the anchor body 152, as illustrated in FIGS. 3-5. In another embodiment, at least some of the protruding elements 150 are not displaced from each other along the longitudinal axis 170. Rather, some of the protruding elements 150 are aligned with a plane 172 that extends perpendicular to the longitudinal axis 170.

Figure 7:
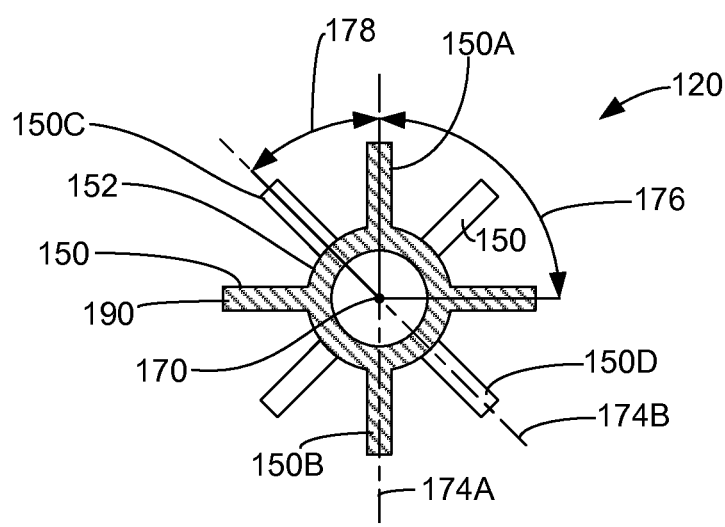
FIG. 7 is a front cross-sectional view of an anchor in accordance with embodiments of the invention.

In one embodiment, the protruding elements 150 are angularly aligned such that at least some of the protruding elements 150 are positioned in the same radial plane, such as protruding elements 150A and 150B that are aligned with the radial plane 174A, which extends through the longitudinal axis 170, as shown in FIG. 7.

In one embodiment, the protruding elements 150 are angularly displaced from each other by an angle 176, as shown in FIG. 7. The angle 176 can be selected based on the type of protruding element 150 being used, the number of protruding elements 150, the type of tissue in which the protruding elements 150 are to be embedded and other factors. Exemplary angles 176 include angles that result in the equal angular displacement of the protruding elements 150 that are in the same plane 172 that is perpendicular to the longitudinal axis 170, such as 90 degrees for the exemplary embodiment illustrated in FIG. 7. In one embodiment, the angles 176 between the protruding elements are non-uniform. This may be useful when there is a side of the lead body 110 that will be in close proximity to tissue that you do not wish to contact with a protruding element 150, for example.

In another embodiment, at least some of the protruding elements 150 that are longitudinally displaced from each other are angularly staggered such that they do not lie in the same radial plane that is in line with the longitudinal axis. For instance, one or more protruding elements 150A and 150B may be positioned in the radial plane 174A while one or more other protruding elements 150C and 150D, which are longitudinally displaced from the protruding elements 150A and 150B, are positioned in the radial plane 174B that is angularly displaced from the radial plane 174A by the angle 178, as illustrated in FIG. 7.

In one embodiment, the one or more protruding elements 150 have a proximal end 180 that is attached to the anchor body 152 and a distal end 182 that is displaced from the anchor body 152 and is configured to embed in the tissue of the patient. In one embodiment, the distal end 182 of the protruding element 150 is angled toward a proximal side 184 of the anchor 120 corresponding to the proximal end 106 of the electrode lead 104, as illustrated by protruding element 150A of FIG. 8. In accordance with another embodiment, the distal end 182 of the protruding element 150 is angled toward the distal side 186 of the anchor 120 corresponding to the distal end 114 of the electrode lead 104, as illustrated by protruding element 150B in FIG. 8. In accordance with another embodiment, the anchor 120 includes a combination of protruding elements 150 having distal ends 182 that are angled toward the proximal side 184 and the distal side 186 of the anchor 120, as shown in FIG. 8.

Additional embodiments of the anchor 120 include various combinations of the above-described embodiments and one or more of the embodiments of the protruding elements 150 described below. In one embodiment, the protruding elements 150 extend radially from the anchor body 152 and operate to secure the position of the electrode lead 104 relative to the tissue in which it is embedded. The radially extending protruding element or elements 150 of the anchor 120 resist movement of the electrode lead 104 in the longitudinal direction defined by the longitudinal axis 170 of the electrode lead 104 relative to the tissue in which the electrode lead 104 is embedded. Embodiments of the protruding elements 150 can also operate to inhibit or prevent the electrode lead 104 from twisting relative to the tissue in which it is embedded.

In one embodiment, the protruding element 150 is flexible and can be compressed radially toward the anchor body 152. This compressibility of the protruding element or elements 150 allows the anchor 120 to be received within an introducer for deployment into the desired tissue of the patient. Additionally, this flexibility can provide a stress relief from forces that drive movement of the anchor 120 relative to the tissue in which the anchor 120 is embedded and can avoid or reduce the likelihood of tearing the tissue. Further, the flexibility of the protruding element 150 can drive the stimulating electrode back to its intended position relative to the tissue in response to small movements of the stimulating electrode 112.

Figure 8:
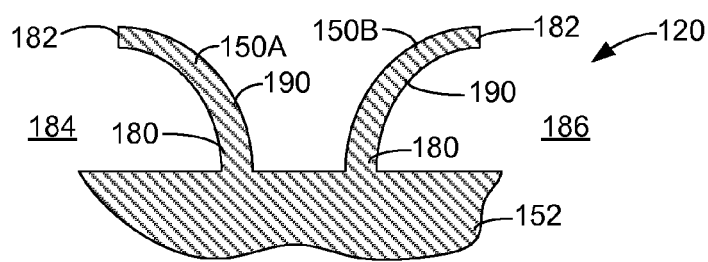
FIG. 8 is a cross-sectional view of a portion of an anchor in accordance with embodiments of the invention.

One embodiment of the protruding element 150 comprises a tine 190, exemplary illustrations of which are shown in FIGS. 3-8. The tine 190 is preferably flexible, but can also be formed to be rigid. In one embodiment, the tine 90 is bowed slightly as shown in FIG. 8.

Figure 9A:
FIG. 9A is a side plan view of an anchor in accordance with embodiments of the invention.
Figure 9B:
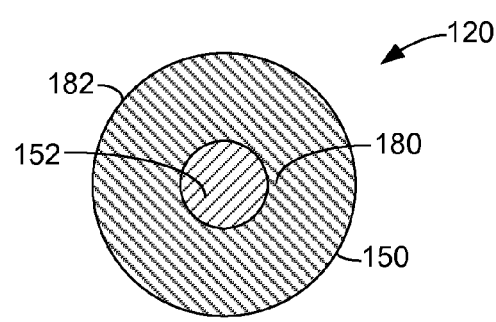
FIG. 9B is a cross-sectional view of the anchor of FIG. 9A taken generally along line B-B.

One embodiment of the protruding element 150 comprises a disk 192 that extends radially from the anchor body 152, as illustrated in the side plan view of FIG. 9A and the cross-sectional view of FIG. 9B taken generally along line B-B of FIG. 9A. In one embodiment, the one or more disks 192 are flexible and hold the electrode lead 104 in the tissue of the patient like plunger seal. The diameter and thickness of the disks 192 can be selected to provide the desired fixation performance.

Figure 10A:
FIG. 10A is a front plan view of an anchor in accordance with embodiments of the invention.
Figure 10B:
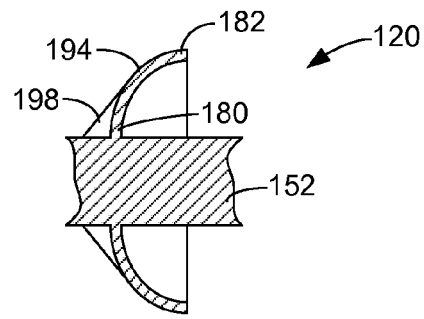
FIG. 10B is a cross-sectional view of the anchor of FIG. 10A taken generally along line B-B.
Figure 11A:
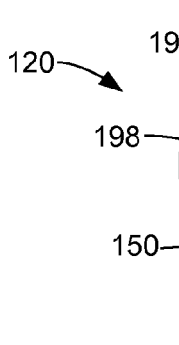
FIG. 11A is a front plan view of an anchor in accordance with embodiments of the invention.
Figure 11B:
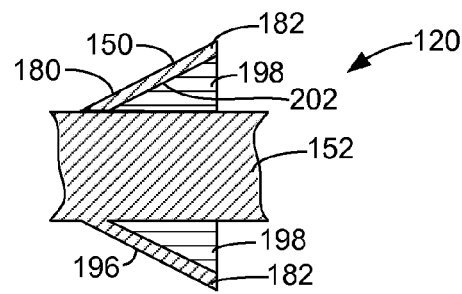
FIG. 11B is a cross-sectional view of the anchor of FIG. 11A taken generally along line B-B.

In another embodiment of the protruding element or elements 150, the anchor 120 comprise an umbrella-shaped cup 194, as illustrated in the front plan view of FIG. 10A and the cross-sectional view of FIG. 10B, which is taken generally along line B-B of FIG. 10A. In another embodiment, the protruding element 150 comprises a cone-shaped cup 196, as illustrated in the front plan view of FIG. 11A and the side-cross sectional view of FIG. 11B, which is generally taken along line B-B of FIG. 11A. The cups 194 and 196 can be reinforced by ribs 198, which limit the amount the cups 194 or 196 flex in response to movement relative to the tissue in which they are embedded. The reinforcing ribs 198 can be formed integrally with the cups 194 or 196, extend between an exterior surface 200 and the anchor body 152 (FIG. 10B), or extend between an interior surface 202 and the anchor body 152 (FIG. 11B).

Figure 12:
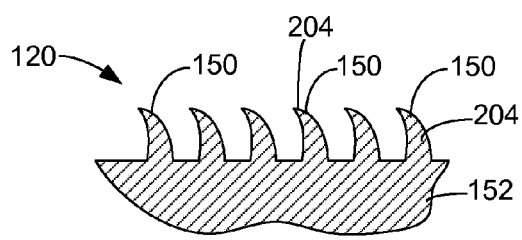
FIG. 12 is a cross-sectional view of a portion of an anchor in accordance with embodiments of the invention.

In one embodiment, the anchor 120 includes one or more protruding elements 150 in the form of barbs 204, as illustrated in the cross-sectional view of a portion of the anchor 120 provided in FIG. 12. The barbs 204 are generally smaller than the tines 190 and are preferably disposed about the surface of the anchor body 152 in greater numbers than the tines 190. The reduced gripping power that the barbs 204 have as a result of the shorter depth to which they extend into the tissue of the patient is preferably offset by greater numbers of barbs 204.

Figure 13:
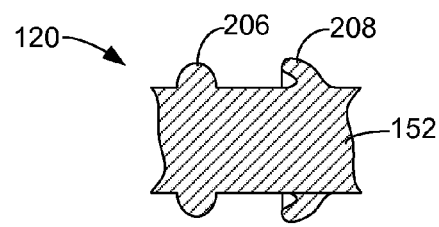
FIG. 13 is a cross-sectional view of a portion of an anchor illustrating various embodiments of the invention.

Another embodiment of the protruding element or elements 150 comprise shaped bumps 206 or ridges 208, as illustrated in the side-cross sectional view of FIG. 13. The bumps 206 generally provide a surface texture to the anchor body 152 that can increase the slip resistance between the anchor 120 and the tissue, in which the anchor 120 is embedded. The ridges 208 can be shaped similarly to the cups 194 and 196 but are generally smaller and do not extend as far radially from the anchor body 152. In one embodiment, the bumps 206 and the ridges 208 are annular and, thus, extend around the circumference of the anchor body 152.

Figure 14:
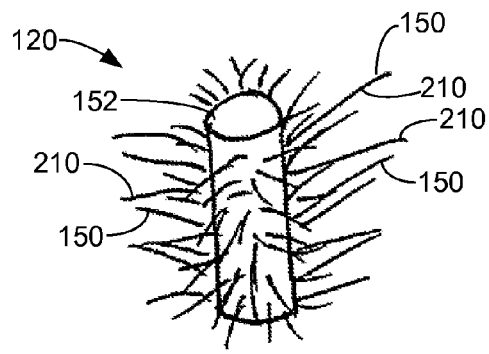
FIGS. 14 and 15 are isometric views of anchors in accordance with embodiments of the invention.

FIG. 14 is an isometric view of an anchor 120 in accordance with another embodiment of the invention, in which the protruding elements 150 are in the form of bristles or brush-like protrusions 210. The bristles 210 can be similar to those typically found in test tube or bottle brushes. Embodiments of the protruding elements 210 include orienting the bristles such that they are substantially perpendicular to the longitudinal axis 170, or angling the protruding elements 210 toward the proximal side 184, and/or the distal side 186 of the anchor 120.

Figure 15:
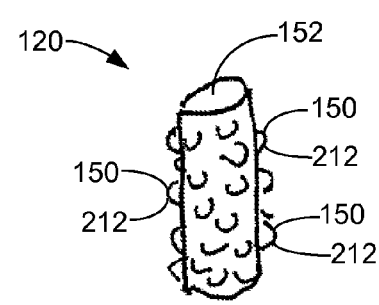

FIG. 15 is an isometric view of an anchor 120 in accordance with another embodiment of the invention, in which the protruding elements 150 are in the form of fiber loops 212 that are disposed about the exterior surface of the anchor body 152. The tissue, in which the anchor 120 is embedded, grows around and through the fibrous loops to secure the anchor 120 to the tissue. In one embodiment, the fibrous loops 212 are similar to Velcro® or DuoLock® like material, or are of a hook and loop design.

Figure 16A:
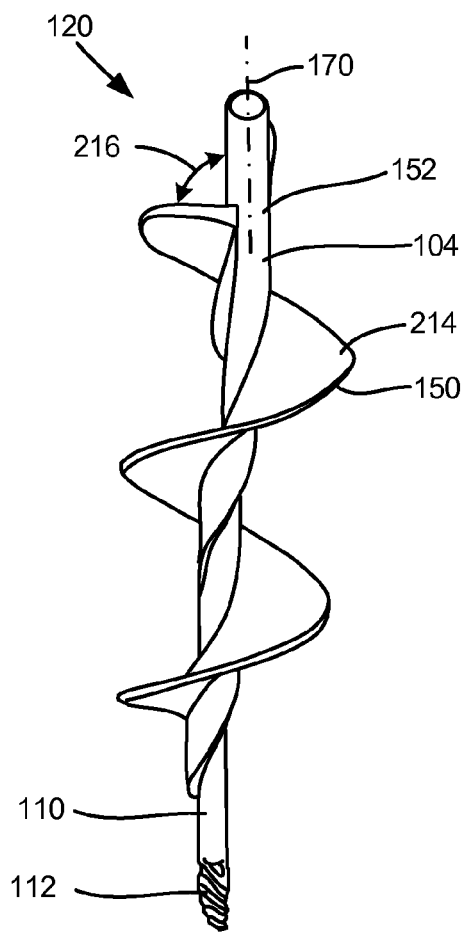
FIGS. 16A and 16B are isometric views of anchors in accordance with embodiments of the invention.
Figure 16B:
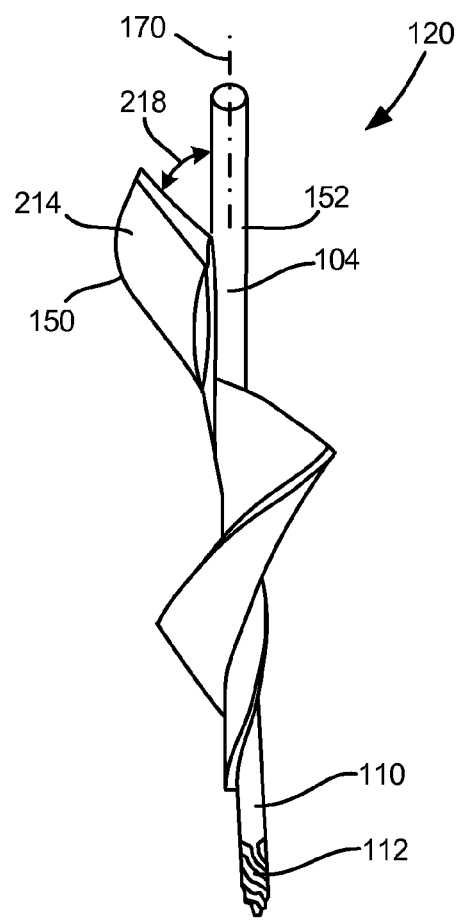

FIGS. 16A and 16B are isometric views of anchors 120, in which the protruding elements 150 comprises a spiraling thread 214. The thread 214 operates like a screw that can be screwed into the tissue of the patient by rotating the anchor 120 in the appropriate direction. In one embodiment, the thread 214 extends radially from the anchor body 152 at an angle 216 that is approximately perpendicular to the longitudinal axis 170 of the anchor body 152, as shown in FIG. 16A. In accordance with another embodiment, the thread 214 extends from the anchor body 152 at an acute angle 218 relative to the longitudinal axis 170. In one embodiment, the threads 214 are formed of a rigid plastic or other biocompatible material. In another embodiment, the threads 214 are formed of a flexible material that allows the threads 214 to flex with motion of the tissue.

Figure 17:
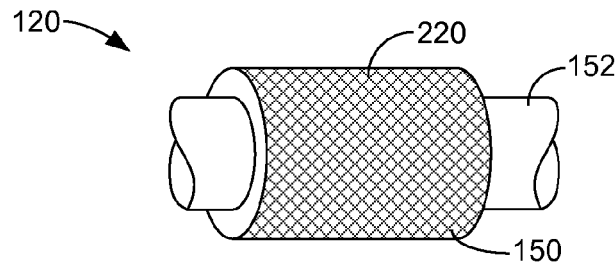
FIG. 17 is an isometric view of an anchor in accordance with embodiments of the invention.

FIG. 17 is an isometric view of an anchor 120 in accordance with another embodiment of the invention, in which the protruding element 150 is in the form of a mesh sleeve 220. The mesh sleeve 220 preferably extends around the circumference of the anchor body 152 and can be concentric thereto. The size of the openings or pores of the mesh sleeve 220 are preferably sufficient to allow tissue in-growth and fixation within the surrounding tissue. The mesh can be made from polypropylene, for example.

Figure 18:
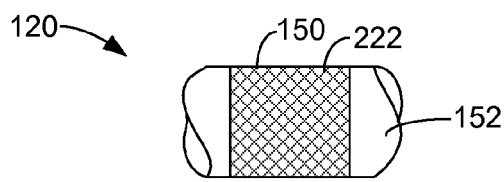
FIG. 18 is a front plan view of an anchor in accordance with embodiments of the invention.

In accordance with another embodiment, a mesh material 222 is integrally formed with the anchor body 152, as illustrated in FIG. 18.

Figure 19:
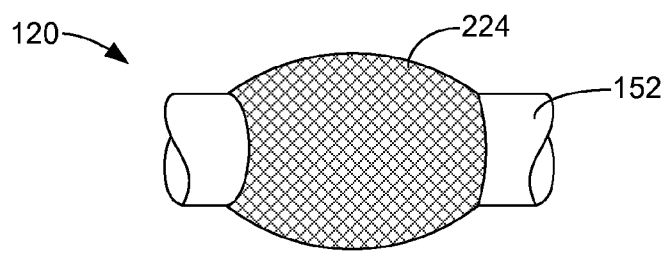
FIG. 19 is a front plan view of an anchor in an expanded state.

In one embodiment of the anchor 120, the anchor body 152 comprises an expandable stent like mesh 224 that is formed of a flexible material or plastic, as shown in the side plan view of FIG. 19, in which the expandable stent like mesh 224 is shown in an expanded state. During the implantation of the anchor 120 in the patient, the expandable stent like mesh 224 is placed in a compact state, similar to that illustrated in FIG. 18. Once the anchor 120 is in the desired position within the tissue of the patient, the expandable stent like mesh 224 can be expanded in accordance with conventional techniques into the tissue of the patient. The expansion of the stent 224 provides immediate resistance to movement of the anchor 120 relative to the tissue. Over time, the tissue of the patient is allowed to grow within the pores of the mesh material, which further secures the anchor 120 to the tissue of the patient.

In accordance with another embodiment of the invention, the protruding elements 150 of the anchor 120 are either partially or completely covered by a material that allows for the temporary repositioning of the anchor 120 relative to the tissue of the patient. This is particularly useful where the protruding elements are not compatible with an introducer or are relatively inflexible.

Figure 20A:
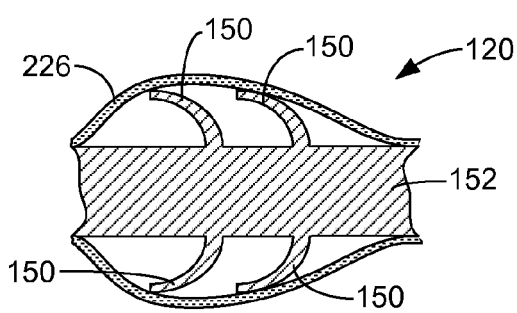
FIGS. 20A and 20B illustrate a temporary anchor covering in accordance with embodiments of the invention.
Figure 20B:
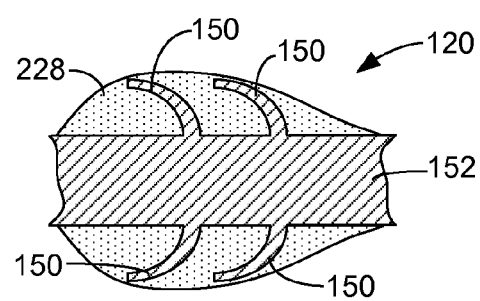

In one embodiment, the protruding elements 150 of the anchor 120 are wrapped in a sheath 226, as shown in the side cross-sectional view of FIG. 20A. The sheath 226 prevents the protruding elements 150 from gripping the tissue of the patient as the anchor 120 is moved in either the forward or rearward direction along the longitudinal axis 170 of the anchor body 152. In one embodiment, the sheath operates to compress the protruding elements 150 toward the anchor body 152, which reduces the cross-sectional area of the anchor 120 and allows for easier insertion and repositioning of the anchor 120 within the tissue of the patient.

In one embodiment, the sheath 226 can be removed after the anchor 120 or stimulating electrode 112 is placed in the desired position. In one embodiment, the sheath 226 includes a longitudinal slit that simplifies its removal. In another embodiment, a wire or other component is used to pull out the sheath 226 or generate a longitudinal slit in sheath 226 after the implantation of the electrode anchor body 152. After the sheath is removed or absorbed by the patient, the protruding elements spring open to an expanded position and embed into the tissue of the patient.

In another embodiment, the sheath 226 is formed of a material that is absorbable by the patient. Once the anchor body 120 or the stimulating electrode 112 is place in the desired position within the patient, the sheath 226 is absorbed by the body and the protruding elements 150 are allowed to become embedded within tissue of the patient.

In accordance with another embodiment, an absorbable material 228 is positioned at least about the protruding elements 150 to prevent the protruding elements 150 from snagging the tissue of the patient. The material 228 allows the anchor 120 to be moved in either direction along the longitudinal axis 170 within the tissue of the patient. After the anchor 120 is placed in the desired position within the tissue of the patient, the absorbable material gets absorbed by the patient over time and the protruding elements become embedded in the tissue of the patient.

Figure 21A:
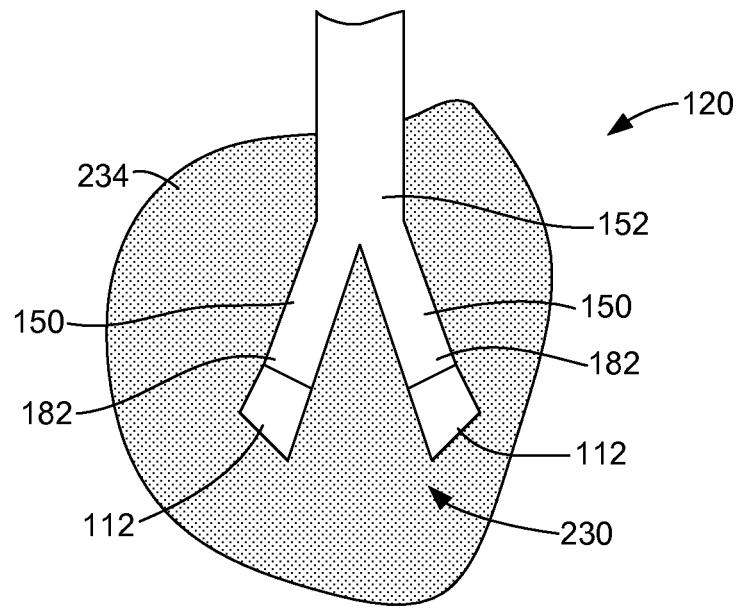
FIGS. 21A and 21B are simplified top plan views of one embodiment of an anchor in opened and closed positions, respectively.
Figure 21B:
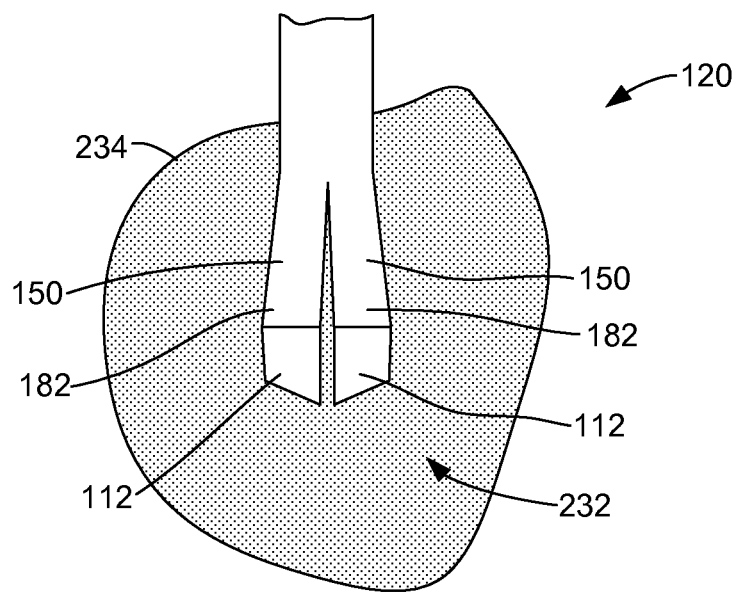

The anchor 120 illustrated in the top plan views of FIGS. 21A and 21B comprises a pair of protruding elements 150 that can be placed in an expanded position 230, which is illustrated in FIG. 21A, and a closed or clamping position 232, which is illustrated in FIG. 21B. Initially, the anchor 120 is driven into the tissue 234 of the patient while in the expanded position 230. Once inserted into the tissue as desired, the protruding elements 150 of the anchor 120 are brought together to the clamping position 232 and the tissue is pinched between the protruding elements 150. When in the clamping position, the protruding elements 150 grip the tissue 234 and secure the anchor 120 to the tissue 234. In one embodiment, one or more stimulating electrodes 112 are located at the distal end 182 of at least one of the protruding elements 150 and are configured to apply electrical stimulation to the tissue 234 that is generated by the control unit 102 described above.

Figure 22A:
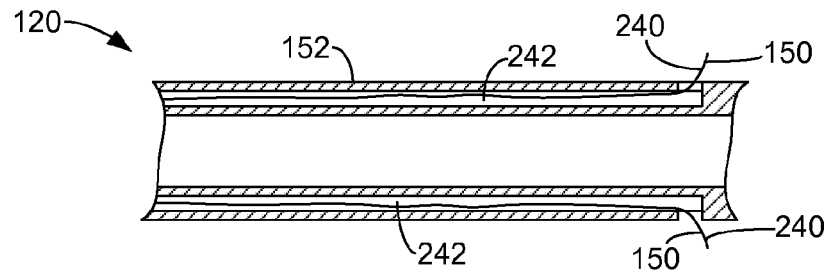
FIGS. 22A-22C illustrate various stages of deployment of a protruding element of an anchor in accordance with embodiments of the invention.
Figure 22B:
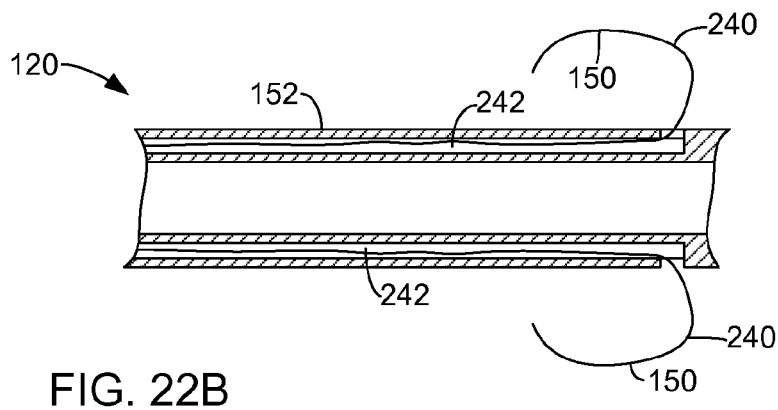
Figure 22C:
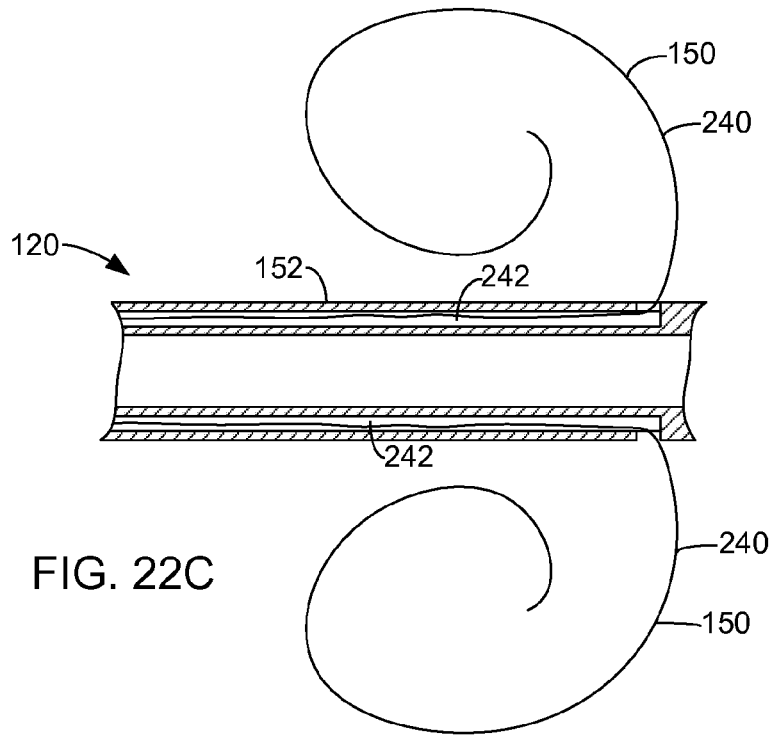
Figure 23:
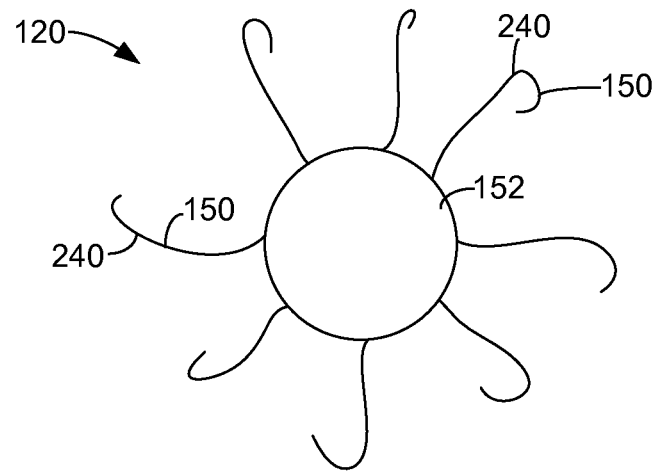
FIGS. 23 and 24 are simplified on-axis views of various embodiments of the anchor shown in FIGS. 22A-22C.
Figure 24:
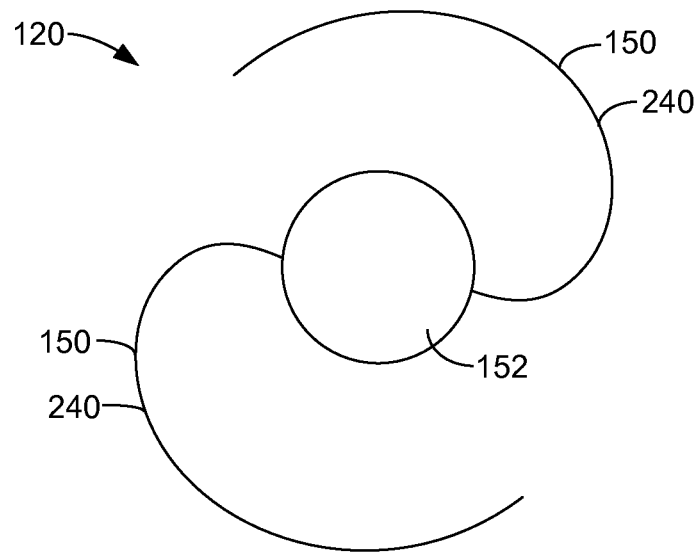

FIGS. 22A-C illustrate an anchor 120 in accordance with another embodiment of the invention, in which the protruding element or elements 150 comprise a fine wire 240 that extends out of a lumen 242 that is formed in the anchor body 152. In one embodiment, the wire 240 is initially in a retracted position, shown in FIG. 22A, in which the wire 240 is either slightly extended out of the lumen 242 (as shown) or fully retracted within the lumen 242. This arrangement allows the anchor 120 to be fed into the tissue of the patient. Once the anchor 120 is in the desired position within the tissue of the patient, the wire 240 can be extended out of the lumen 242 and into the tissue, as illustrated in FIG. 22B. In one embodiment, the wire 240 coils as it is fed into the tissue of the patient, as illustrated in FIG. 22C. In one embodiment, the wire 240 is formed of a memory shaped material, such as nickel titanium (i.e., NITINOL), that forces the wire 240 to follow a coil trajectory through the surrounding tissue of the patient as it is extended from the lumen 242. Embodiments of the anchor 120 include one or more wires 240. The wires 240 can be angularly displaced about the surface of the anchor body 120, as illustrated in the on-axis view of FIG. 23. In one embodiment, the wires 240 are configured to coil around the anchor body 152, as illustrated in the on-axis view of FIG. 24.

Figure 25A:
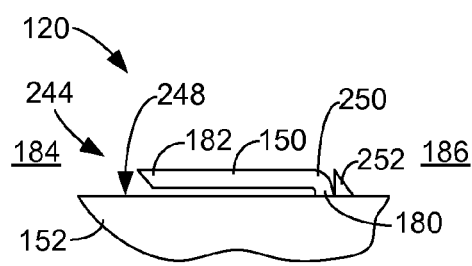
FIGS. 25A and 25B are simplified side views of a hinged anchor respectively in retracted and extended positions in accordance with embodiments of the invention.
Figure 25B:
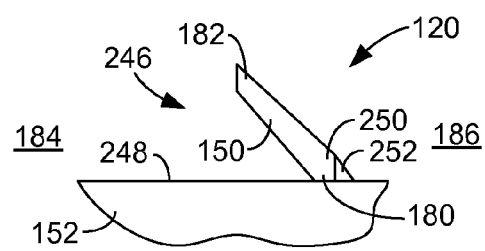

Another embodiment of the anchor 120 of the present invention comprises one or more protruding elements 150 that are configured to have a retracted position, in which the distal end 182 of the protruding element 150 is located in close proximity to the anchor body 152, and an extended position, in which the distal end 182 is displaced radially from the anchor body 152. FIGS. 25A and 25B are side plan views of an embodiment of a protruding element 150 respectively in a retracted position 244 and an extended position 246. When in the retracted position 244, the distal end 182 of the protruding element 150 lies in close proximity to the exterior surface 248 of the anchor body 152. In one embodiment, the protruding element 150 is flexible and is configured to bend at a portion 250 that is adjacent to the proximal end 180. A protruding element 150 can move to this retracted position 244 automatically in response to the feeding of the anchor 120 through the tissue of the patient or by placing the anchor 120 in a tube of an introducer, for example.

Once the anchor 120 is positioned as desired in the tissue of the patient, the anchor body 152 can be pulled toward the proximal side 184. During this movement of the anchor body 120, the distal end 182 of the protruding element 150 snags a portion of the tissue of the patient and the protruding element 150 is driven to the extended position 246 shown in FIG. 25B. With only a slight movement of the anchor body 152 toward the proximal side 184, the protruding element 150 can reach the fully extended position 246. In one embodiment, a stop member 252 is positioned to limit the distance that the distal end 182 of the protruding element 150 can move toward the distal side 186. Thus, the stop member 252 defines the fully extended position 246 for the protruding element 150.

Figure 26A:
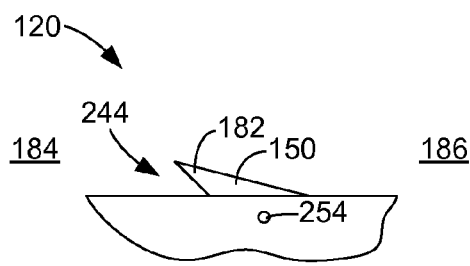
FIGS. 26A and 26B are simplified side views of a hinged anchor respectively in retracted and extended positions in accordance with embodiments of the invention.
Figure 26B:
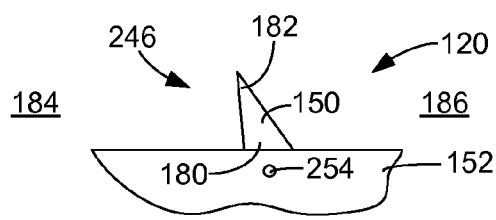

FIGS. 26A and 26B respectively illustrate another embodiment of a protruding element 150 having a retracted position 244 and an extended position 246. In accordance with one embodiment, the protruding element 150 is coupled to the anchor body 152 by a hinge 254. The protruding element 150 is allowed to pivot about the hinge 254 between the retracted position 244 shown in FIG. 26A and the extended position 246 shown in FIG. 26B. As with the embodiment of the protruding element 150 described above with regard to FIGS. 25A and 25B, the protruding element 150 shown in FIGS. 26A and 26B moves from the retracted position 244 to the extended position 246 in response to movement of the anchor body 152 toward the proximal side 184 or during the slight withdrawal of the anchor 120 from the tissue of the patient.

Figure 27:
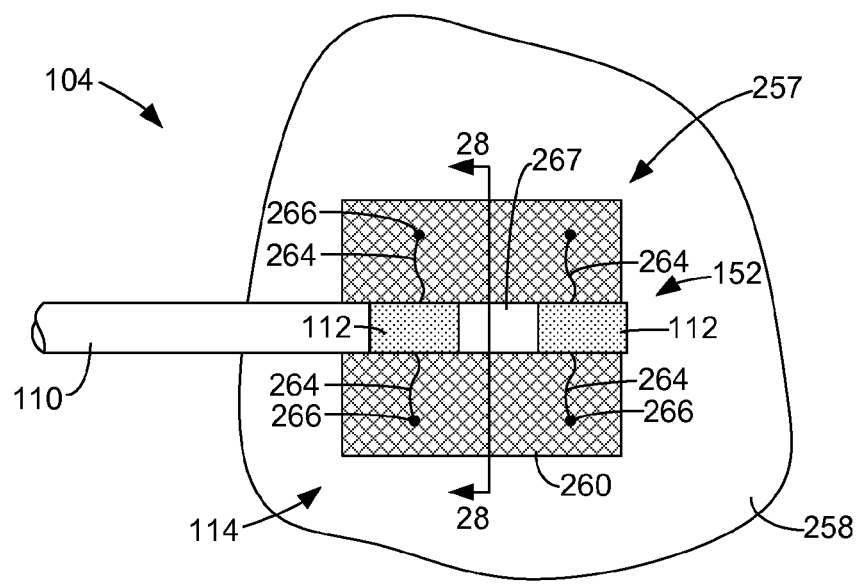
FIG. 27 is a simplified side view of an electrode lead comprising a fixation component in accordance with embodiments of the invention.
Figure 28:
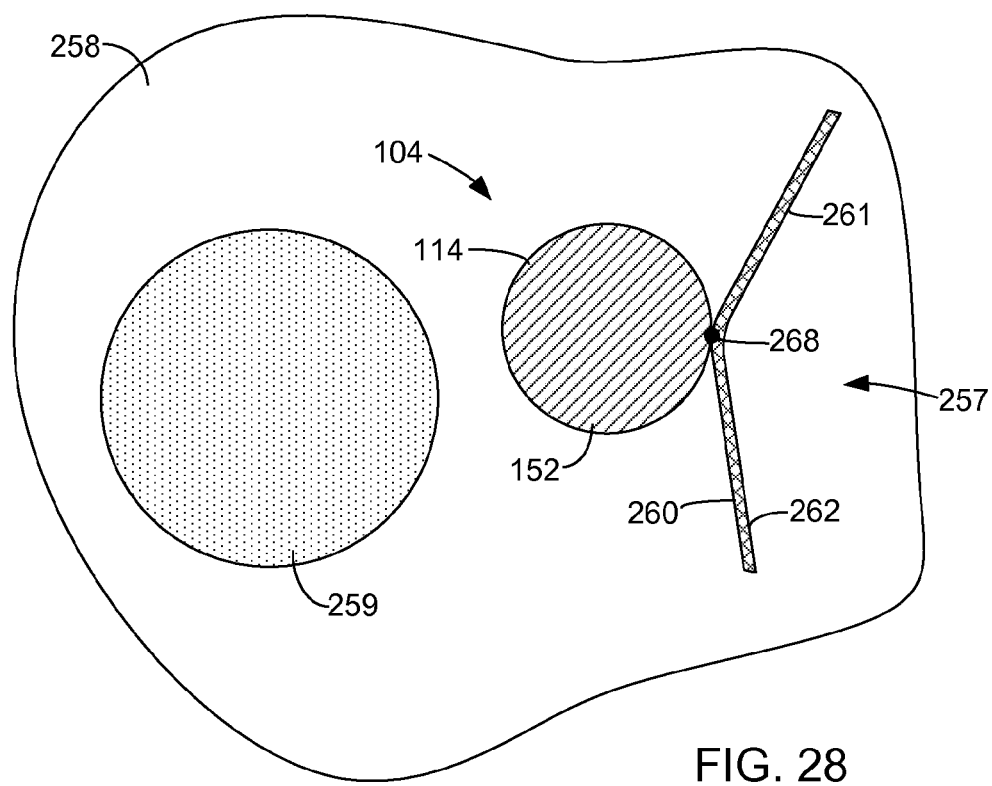
FIG. 28 is a side cross-sectional view of the electrode lead of FIG. 27 taken generally along line 28-28.

FIG. 27 illustrates a simplified side view of a distal end 114 of an electrode lead 104 having a lead body 110 that includes an anchor 257, in accordance with embodiments of the invention, that is implanted in tissue 258 of the patient. FIG. 28 provides a cross-sectional view of the anchor 257 taken generally along line 28-28 of FIG. 27 and illustrates the implantation of the distal end 114 of the electrode adjacent a structure 259 of the patient.

As discussed above, one embodiment of the electrode lead 104 comprises one or more electrodes 112, each located at a distal end 114 of the lead body 110. The electrodes 112 may be separated by an insulating element 267, which may comprise the lead body 110.

One embodiment of the anchor 257 comprises an anchor body 152 in accordance with the embodiments described above, such as the lead body 110 (FIG. 27), and a section of mesh 260 attached to the anchor body 152. In one embodiment, the anchor 257 is located at the distal end 114 of the electrode lead 104. The bio-compatible mesh 260 is preferably an open matrix mesh, such as a mesh constructed of polypropylene monofilament. In one embodiment, the mesh 260 comprises one or more mesh sections or wings, such as wings 261 and 262.

In one embodiment, the mesh 260 has a compact state and an expanded state. In general, at least a portion of the mesh 260 is displaced a greater distance from the anchor body 152 when in the expanded state than when in the compact state. The anchor 257 is generally in a form suitable for implantation in the tissue 258 when the mesh 260 is in the compact state and performs its anchoring function in the tissue 258 when the mesh 260 is in the expanded state, such as described above with regard to FIG. 19.

In one embodiment, the mesh 260 has a shape memory that drives the mesh to a preset expanded, quiescent shape, in which at least a portion of the mesh 260 extends away from the anchor body 152 and into the surrounding tissue 258. As used herein, the "quiescent shape" of the mesh 260 is one in which the mesh will naturally return to after being deformed, such as when compressed into a compact state.

In one embodiment, the expanded state of the mesh wings 261 and 262 is one in which the wings 261 and 262 are displaced from each other, such as illustrated FIG. 28. Thus, one embodiment of the mesh 260 has a shape memory that encourages separation of the one or more wings, such as wings 261 and 262, within the tissue 258.

In one embodiment, the anchor 257 is configured to deliver electrical signals from the control unit to the tissue 258. In one embodiment, the mesh 260 comprises the one or more electrodes 112 that are used to deliver electrical signals to the tissue 258. In one embodiment, one or more conductive fibers 264 (FIG. 27) are attached to the mesh 260 and conduct electrical signals from one or more of the electrodes 112 of the lead body (FIG. 27), or the control unit 102, into the tissue 258. In one embodiment, the conductive fivers 264 are electrically insulated from the tissue 258 and conduct the electrical signals to one or more electrically conductive nodes or electrodes 266 that are attached to the mesh 260 and deliver the electrical signals to the tissue 258.

A portion of the mesh 260 is attached to the distal end 114 of the electrode lead 104 at a location 268. Exemplary means for attaching the mesh 260 to the electrode lead 104 include sutures, glue, anchors, or other suitable bio-compatible methods. In one embodiment, the attachment location 268 comprises a central portion of the mesh 260. As a result, one embodiment of the anchor 257 comprises at least two wings of mesh 261 and 262 that extend from the distal end of the electrode lead 104 at the connection location 268.

Figure 29:
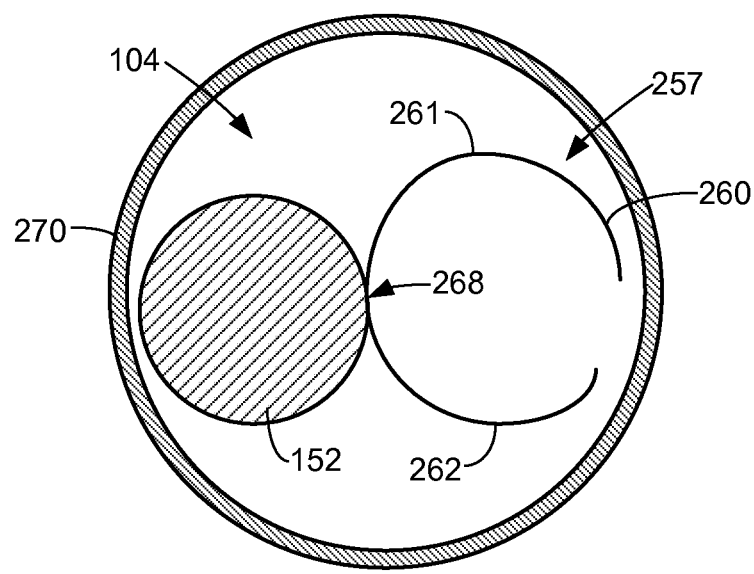
FIG. 29 is a front cross-sectional view of a distal end of an electrode lead installed within a trocar.

FIG. 29 is a simplified cross-sectional view of the distal end 114 of the electrode lead 104 having the anchor 257 installed in a delivery trocar 270 that is used to implant the electrode lead 104 in the desired tissue 258 of the patient. In one embodiment, the mesh 260 of the anchor 257 is placed in the compact state (e.g., rolled up) and installed in the trocar 270. When the anchor 257 is deployed from the trocar 270 into the tissue 258, the mesh 260 expands toward the expanded state or its expanded quiescent shape. Tissue ingrowth secures the mesh 260 to the tissue 258 to anchor the location of the distal end 114 of the electrode lead 104.

When the mesh 260 comprises the wings 261 and 262, the wings 261 and 262 compressed into the compact state, as shown in FIG. 29. In one embodiment, the mesh wings 261 and 262 extend from the connection point 268 away from the distal end 114 of the electrode lead 104. Upon deployment of the distal end 114 of the electrode lead 104 in the desired tissue 258 of the patient, the mesh sections 261 and 262 move toward the preset expanded quiescent shape and into the tissue 258, as shown in FIG. 28. Ingrowth of the tissue 258 into the mesh 260 operates to anchor the mesh 260 to the tissue 258, thereby anchoring the distal end 114 of the electrode lead 104 in the desired position.

In one embodiment, the mesh 260 is deployed in the tissue 258 such that it has a desired orientation relative to the structure 259 of the patient. As a result, the expansion of the mesh 260 can be directed to a side of the electrode lead 104 such that it expands away from the structure 259 or toward the structure 259. For instance, when the structure 259 is in the form of the urethra of the patient, the distal end 114 of the electrode lead 104 can be oriented relative to the urethra 259 such that the mesh 260 is located on a side of the electrode lead 104 that is away from the urethra 259. This prevents fibrosis around the mesh 260 from interfering with the communication of electrical stimulation signals from the electrode lead 104 to the structure 259.

Figure 30:
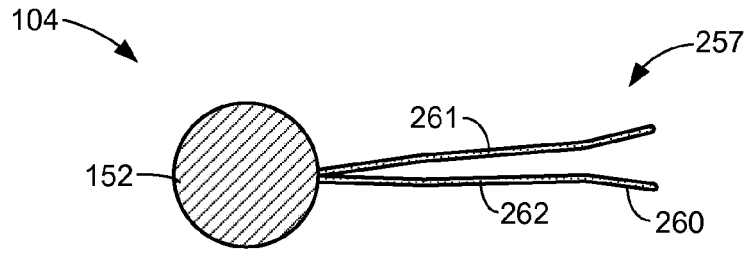
FIG. 30 is a simplified front cross-sectional view of a distal end of an electrode lead comprising a fixation component in accordance with embodiments of the invention.
Figure 31:
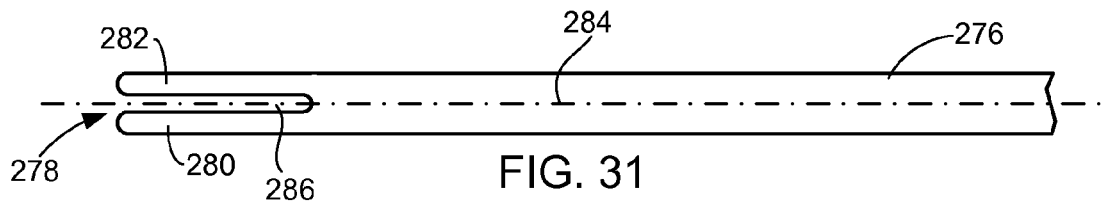
FIG. 31 is a partial side view of an installation tool in accordance with embodiments of the invention.

In one embodiment, the anchor 257 is initially provided in a sterilized and sealed package, in which the mesh 260, such as mesh sections 261 and 262, have a quiescent shape in which they lie substantially flat, as illustrated in the simplified cross-sectional view of FIG. 30. FIG. 31 is a simplified side view of an installation tool 276 in accordance with embodiments of the invention that is used to prepare the anchor 257 for installation within a trocar 270. The tool 276 comprises a forked end 278 that includes prongs 280 and 282 that extend substantially parallel to the longitudinal axis 284 of the tool 276. A gap 286 between the prongs 280 and 282 is configured to receive a distal end 288 of the mesh 260, as illustrated in the simplified cross-sectional view of FIG. 32.

Figure 32:
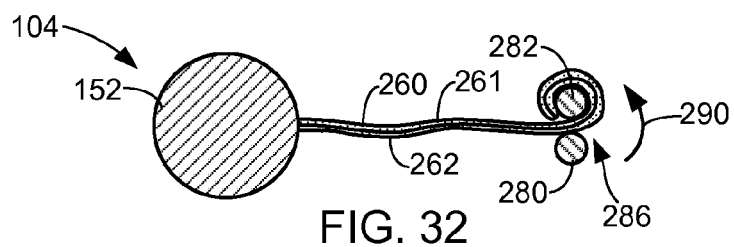
FIGS. 32-34 are simplified front cross-sectional views of the distal end of an electrode lead illustrating a method of installing the electrode lead within a trocar.
Figure 33:
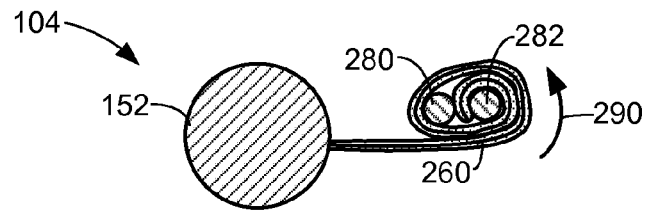
Figure 34:
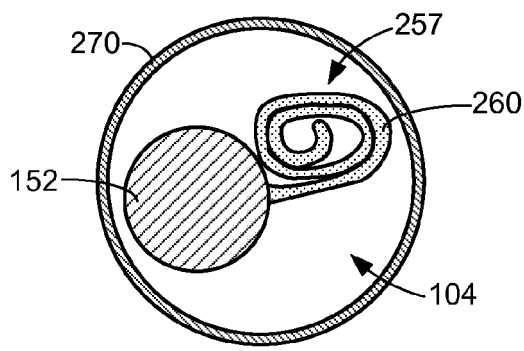

The anchor 257 is prepared for installation within a trocar 270 by placing the end 288 of the mesh 260 through the gap 286 and rotating the tool 276, such as in the direction indicated by arrow 290, to roll up the mesh 260, as illustrated in simplified front cross-sectional views of FIGS. 32 and 33. Once the mesh 260 has been rolled up into a compact state, the distal end 114 of the electrode lead 104 and the anchor 257 can be installed in a trocar 270, as illustrated in the simplified cross-sectional view of FIG. 34. The end 278 of the tool 276 is disengaged from the mesh 260 either prior to or after the insertion of the distal end 114 within the trocar 270. When the distal end 114 of the electrode lead 104 is deployed into the desired tissue 258 of the patient using the trocar 270, the mesh 260 expands toward its expanded quiescent shape within the tissue 258, as discussed above.

Figure 35:
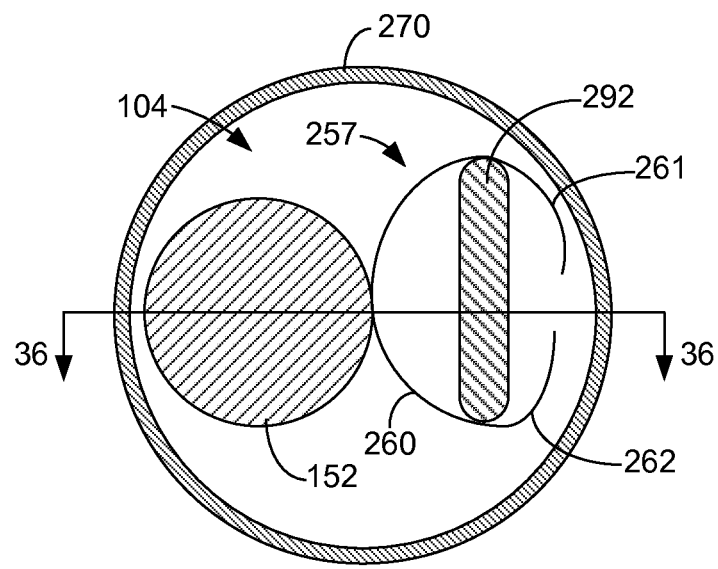
FIG. 35 is a simplified front cross-sectional view of an electrode lead installed within a trocar along with a tool in accordance with embodiments of the invention.
Figure 36:
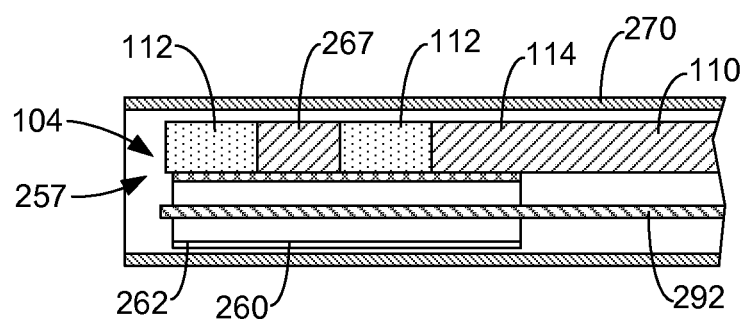
FIG. 36 is a side cross-sectional view of FIG. 35 taken generally along line 36-36.

FIGS. 35 and 36 respectively are front and side cross-sectional views of a distal end 114 of the electrode lead 104 comprising the anchor 257 installed within a trocar 270, in accordance with embodiments of the invention. A tool 292 is installed in the trocar 270 to aid in the deployment of the mesh wings 261 and 262.

In one embodiment, the tool 292 operates to separate the mesh wings 261 and 262 and prevent their entanglement within the trocar 270.

In one embodiment, the tool 292 is configured to cause or assist in the expansion of the mesh wings 261 and 262 into the tissue 258 after deployment of the distal end 114 into the tissue 258. In one embodiment, once the distal end 114 of the electrode lead 104 held in the trocar 270 is located at the desired position within the tissue 258 of the patient, the trocar 270 is partially retracted, as illustrated in the side cross-sectional view of FIG. 37. In one embodiment, the cross-sectional width of the end 284 of the tool 292 is expanded, which drives the mesh wings 261 and 262 away from each other within the tissue 258, as illustrated in FIG. 38. The distal end 294 of the tool 292 can then be withdrawn into the trocar 270 and removed from the patient through the trocar 270 to complete the implantation of the distal end 114 of the electrode lead 104 within the tissue 258 of the patient, as illustrated in the cross-sectional view of FIG. 39. In one embodiment, the cross-sectional width of the end 294 of the tool 292 is reduced prior to its withdrawal from the patient.

In one embodiment, the tool 292 comprises a scissor-like mechanism that expands the effective width of the distal end 294.

Figure 40:
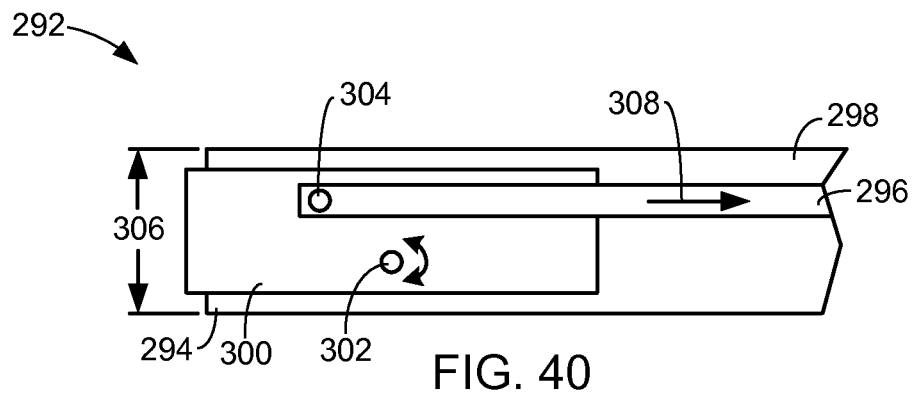
FIGS. 40-42 are simplified side views of an electrode lead installation tool in accordance with embodiments of the invention.
Figure 41:
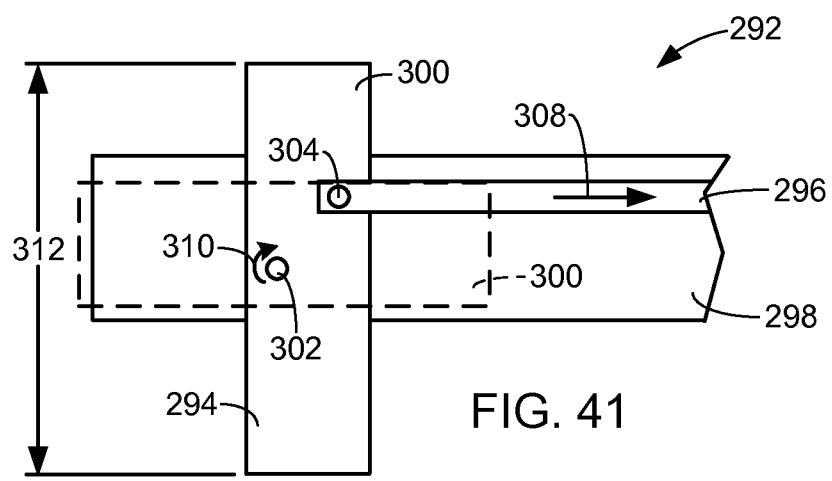
Figure 42:
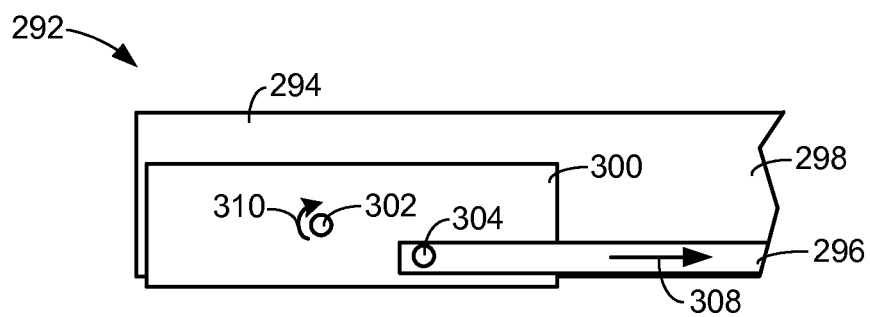

FIGS. 40-42 are simplified side views of a tool 292 in accordance with embodiments of the invention. In one embodiment, the tool 292 comprises first and second elongated components 296 and 298 that are respectively coupled to a third component 300 through hinges 302 and 304. The initial width 306 of the tool 292 allows the tool 292 to be received within the trocar 270, as shown in FIGS. 35 and 36. Following the retraction of the trocar 270 (FIG. 37), component 296 is moved relative to component 298, such as, for example, in the direction indicated by arrow 308. The displacement of the hinge 304 from the hinge 302 in the widthwise direction causes the component 300 to pivot about the hinge 302 relative to the component 298 in the direction indicated by arrow 310 to an expanded position, as shown in FIG. 41. The width 312 of the distal end 294 of the tool 292 in the expanded position is significantly greater than the width 306. This expansion of the width of the distal end 294 drives the expansion of the mesh wings 261 and 262, as illustrated in FIG. 38.

After the mesh wings 261 and 262 have been expanded through the expansion of the width of the distal end 294 of the tool 292, the component 296 can be further moved relative to the component 298 in a direction indicated by arrow 308 to place the distal end 294 in a compacted state (FIG. 42), in which the tool 292 may either be received again within the trocar 270, or otherwise removed from the patient, while leaving the distal end 114 of the electrode lead 104 in the desired location within the tissue 258 of the patient.

Figure 43:
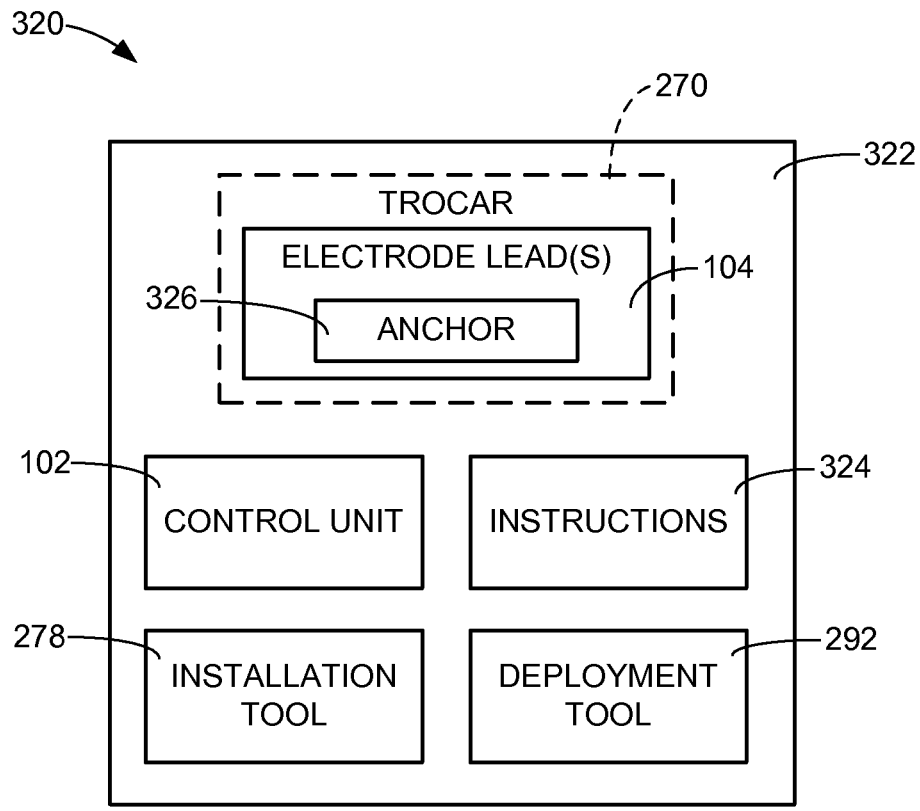
FIG. 43 is a block diagram of a kit in accordance with embodiments of the invention.

Additional embodiments of the invention are directed to kits that include one or more of the embodiments described above. FIG. 43 illustrates a kit 320 in accordance with embodiments of the invention. In one embodiment, the kit includes a package 322 containing components including one or more electrode leads 104 in accordance with one or more of the embodiments described above. In one embodiment, the kit 320 includes the control unit 102. In one embodiment, the kit includes instructions 326 for installing the one or more electrode leads 104 in the patient. In one embodiment, the instructions 324 include instructions for installing the control unit 102.

In one embodiment, the one or more electrode leads 104 in the kit 320 include an anchor 326 in accordance with one or more of the embodiments described above, such as anchor 120 or 257. In accordance with one embodiment, the distal end 114 of the one or more electrode leads are provided pre-installed in a trocar 270. In accordance with one embodiment, one or more tools, such as installation tool 278 or deployment tool 292, are provided in the kit 320. Embodiments of the instructions 324 include instructions for implanting the distal end 114 of the electrode lead 104 within tissue 258 of the patient using the trocar 270, tool 278 and/or tool 292. Such instructions include instructions describing one or more of the method steps discussed above with reference to FIGS. 32-42.

Although the present invention has been described with reference to preferred embodiments, workers skilled in the art will recognize that changes may be made in form and detail without departing from the spirit and scope of the invention.

What is claimed is:

1. An electrode lead for implantation in a patient comprising:
   a lead body having a proximal end, a distal end and a longitudinal axis;
   a stimulating electrode attached to the lead body at the distal end; and
   an anchor at the distal end of the lead body comprising one or more annular protruding elements concentric to the longitudinal axis and including a proximal end attached to the lead body and a distal end displaced from the lead body, wherein the one or more annular protruding elements each comprise an umbrella-shaped or cone-shaped cup member extending continuously between the proximal and distal ends of the element and around the lead body having an interior surface that faces the lead body, an exterior surface that faces away from the lead body, and at least one rib extending from the interior surface to the lead body.

2. The electrode lead of claim 1, wherein the at least one rib is parallel to the longitudinal axis.

3. The electrode lead of claim 1, wherein the distal end of each of the one or more annular protruding elements is displaced along the longitudinal axis from the proximal end.

4. The electrode lead of claim 1, wherein the distal end of each of the one or more annular protruding elements is radially displaced from the lead body relative to the longitudinal axis.

5. The electrode lead of claim 4, wherein the distal end of each of the one or more annular protruding elements forms a ring around the lead body.

6. The electrode lead of claim 5, wherein each of the one or more protruding elements terminates at the distal end.

* * * * *